(12) United States Patent
Nuccitelli et al.

(10) Patent No.: US 10,391,125 B2
(45) Date of Patent: *Aug. 27, 2019

(54) METHODS AND DEVICES FOR STIMULATING AN IMMUNE RESPONSE USING NANOSECOND PULSED ELECTRIC FIELDS

(71) Applicant: Pulse Biosciences, Inc., Hayward, CA (US)

(72) Inventors: Richard Lee Nuccitelli, Millbrae, CA (US); Pamela S. Nuccitelli, Millbrae, CA (US); Joanne Lum, San Francisco, CA (US); Kaying Lui, Millbrae, CA (US); Brian G. Athos, San Francisco, CA (US); Mark P. Kreis, San Francisco, CA (US); Zachary R. Mallon, San Francisco, CA (US); Jon Berridge, Oakland, CA (US)

(73) Assignee: PULSE BIOSCIENCES, INC., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/142,422

(22) Filed: Sep. 26, 2018

(65) Prior Publication Data

US 2019/0022141 A1  Jan. 24, 2019

Related U.S. Application Data

(60) Continuation of application No. 15/873,810, filed on Jan. 17, 2018, now Pat. No. 10,137,152, which is a
(Continued)

(51) Int. Cl.
*A61N 1/36* (2006.01)
*A61K 35/13* (2015.01)
(Continued)

(52) U.S. Cl.
CPC .......... *A61K 35/13* (2013.01); *A61B 18/1477* (2013.01); *A61K 31/704* (2013.01);
(Continued)

(58) Field of Classification Search
USPC .................................................. 607/44, 72
See application file for complete search history.

(56) References Cited

U.S. PATENT DOCUMENTS 6,278,895 B1    8/2001  Bernard
6,326,177 B1 *  12/2001  Schoenbach ....... A61B 18/1206
                                              435/173.7
(Continued)

FOREIGN PATENT DOCUMENTS

WO    2010/011408 A1    1/2010
WO    2014/133870 A1    9/2014
WO    2014/197240 A2    12/2014

OTHER PUBLICATIONS

Barth R. F., "Rat brain tumor models in experimental neuro-oncology: The 9L, C6, T9, F98, RG2 (D47), RT-2 and CNS-1 Gliomas," J Neurooncol., 1998, 36(1): pp. 91-102.
(Continued)

*Primary Examiner* — Nicole F Lavert
(74) *Attorney, Agent, or Firm* — Kilpatrick Townsend & Stockton LLP

(57) ABSTRACT

Nanosecond pulsed electric field (nsPEF) treatments of a tumor are adjusted based on a size and type of the tumor to stimulate an immune response against the tumor and other tumors in the subject. Calreticulin expression on tumor cells can be detected to confirm treatment. An immune response biomarker can be measured, and further nsPEF treatments can be performed if needed to stimulate or further stimulate the immune response. Cancers that have metastasized may be treated by directly treating a tumor that is most accessible. The treatment can be combined with CD47-blocking
(Continued)

antibodies, doxorubicin, CTLA-4-blocking antibodies, and/or PD-1-blocking antibodies. Electrical characteristics of nsPEF treatments can be based on the size, type, and/or strength of tumors and/or a quantity of tumors in the subject.

22 Claims, 23 Drawing Sheets

Related U.S. Application Data continuation of application No. 15/484,550, filed on Apr. 11, 2017, now abandoned, which is a division of application No. 14/805,828, filed on Jul. 22, 2015, now Pat. No. 9,656,066, which is a division of application No. 14/287,957, filed on May 27, 2014, now Pat. No. 9,101,764.

(60) Provisional application No. 61/830,564, filed on Jun. 3, 2013.

(51) Int. Cl.
| | |
|---|---|
| A61B 18/14 | (2006.01) |
| C12N 13/00 | (2006.01) |
| A61N 1/05 | (2006.01) |
| A61N 1/32 | (2006.01) |
| A61K 31/704 | (2006.01) |
| A61K 39/395 | (2006.01) |
| C07K 16/28 | (2006.01) |
| C12N 5/09 | (2010.01) |
| G01N 33/574 | (2006.01) |
| A61N 1/00 | (2006.01) |
| C12N 15/87 | (2006.01) |
| A61B 18/00 | (2006.01) |
| A61N 1/40 | (2006.01) |
| C12M 1/42 | (2006.01) |
| A61N 1/04 | (2006.01) |
| A61N 1/372 | (2006.01) |
| A61K 39/00 | (2006.01) |

(52) U.S. Cl.
CPC ...... *A61K 39/395* (2013.01); *A61K 39/39558* (2013.01); *A61N 1/00* (2013.01); *A61N 1/05* (2013.01); *A61N 1/32* (2013.01); *A61N 1/36* (2013.01); *C07K 16/2803* (2013.01); *C07K 16/2818* (2013.01); *C12N 5/0693* (2013.01); *C12N 13/00* (2013.01); *G01N 33/574* (2013.01); *A61B 2018/0016* (2013.01); *A61B 2018/00613* (2013.01); *A61K 2039/505* (2013.01); *A61N 1/0412* (2013.01); *A61N 1/0424* (2013.01); *A61N 1/327* (2013.01); *A61N 1/37229* (2013.01); *A61N 1/40* (2013.01); *C07K 2317/76* (2013.01); *C12M 35/02* (2013.01); *C12N 15/87* (2013.01); *C12N 2501/599* (2013.01); *C12N 2501/999* (2013.01)

(56) References Cited

U.S. PATENT DOCUMENTS

| | | |
|---|---|---|
| 6,426,666 B1 | 7/2002 | Li et al. |
| 6,831,377 B2 | 12/2004 | Yampolsky et al. |
| 7,483,738 B2 | 1/2009 | Tamarkin et al. |
| 7,565,201 B2 | 7/2009 | Blackmore |
| 7,615,357 B2 | 11/2009 | Maher et al. |
| 7,655,004 B2 | 2/2010 | Long |
| 7,767,433 B2 | 8/2010 | Kuthi |
| 7,824,870 B2 | 11/2010 | Kovalcheck et al. |
| 7,901,929 B2 | 3/2011 | Kuthi |
| 7,901,930 B2 | 3/2011 | Kuthi |
| 8,000,813 B2 | 8/2011 | Schoenbach et al. |
| 8,115,343 B2 | 2/2012 | Sanders |
| 8,120,207 B2 | 2/2012 | Sanders |
| 8,139,339 B2 | 3/2012 | Pakhomov |
| 8,506,564 B2 | 8/2013 | Long et al. |
| 8,512,334 B2 | 8/2013 | Nuccitelli |
| 8,682,426 B2 | 3/2014 | Schoenbach |
| 8,688,227 B2 | 4/2014 | Nuccitelli |
| 8,709,006 B2 | 4/2014 | Juergen |
| 8,798,705 B2 | 8/2014 | Kolb |
| 8,822,222 B2 | 9/2014 | Beebe |
| 8,926,606 B2 | 1/2015 | Davalos et al. |
| 8,948,878 B2 | 2/2015 | Schoenbach |
| 2002/0010491 A1 | 1/2002 | Schoenbach |
| 2002/0146396 A1 | 10/2002 | Albert et al. |
| 2004/0219056 A1 | 11/2004 | Tribelsky et al. |
| 2005/0218423 A1 | 10/2005 | Shimizu et al. |
| 2005/0261672 A1 | 11/2005 | Deem et al. |
| 2006/0062074 A1 | 3/2006 | Gundersen et al. |
| 2006/0216690 A1 | 9/2006 | Maher et al. |
| 2006/0269531 A1 | 11/2006 | Beebe |
| 2006/0281069 A1 | 12/2006 | Maher et al. |
| 2007/0031959 A1 | 2/2007 | Kuthi et al. |
| 2008/0071262 A1 | 3/2008 | Azure et al. |
| 2008/0200912 A1 | 8/2008 | Long |
| 2008/0231337 A1 | 9/2008 | Krishnaswamy et al. |
| 2009/0062792 A1 | 3/2009 | Vakharia et al. |
| 2009/0062795 A1 | 3/2009 | Vakharia et al. |
| 2009/0198231 A1 | 8/2009 | Esser |
| 2009/0299417 A1 | 12/2009 | Schoenbach |
| 2010/0038971 A1 | 2/2010 | Sanders et al. |
| 2010/0130972 A1 | 5/2010 | Yambor et al. |
| 2010/0152725 A1 | 6/2010 | Pearson et al. |
| 2010/0222734 A1 | 9/2010 | Jayes et al. |
| 2010/0240995 A1 | 9/2010 | Nuccitelli |
| 2010/0256630 A1 | 10/2010 | Hamilton et al. |
| 2010/0261994 A1 | 10/2010 | Davalos et al. |
| 2010/0274327 A1 | 10/2010 | Carroll et al. |
| 2010/0278401 A1 | 11/2010 | Schoenbach |
| 2011/0092973 A1 | 4/2011 | Nuccitelli |
| 2011/0106221 A1 | 5/2011 | Neal, II et al. |
| 2011/0288545 A1 | 11/2011 | Beebe |
| 2011/0318319 A1 | 12/2011 | Hargrave |
| 2012/0035511 A1 | 2/2012 | Schoenbach |
| 2012/0059255 A1 | 3/2012 | Paul et al. |
| 2012/0089209 A1 | 4/2012 | Schoenbach |
| 2012/0109122 A1 | 5/2012 | Arena et al. |
| 2012/0109263 A1 | 5/2012 | Kolb et al. |
| 2012/0315704 A1 | 12/2012 | Beebe |
| 2013/0041443 A1 | 2/2013 | Weissberg |
| 2013/0150935 A1 | 6/2013 | Weissberg |
| 2013/0172884 A1 | 7/2013 | Schoenbach |
| 2013/0260435 A1 | 10/2013 | Pakhomova |
| 2014/0106430 A1 | 4/2014 | Hargrave |
| 2014/0222126 A1 | 8/2014 | Xiao |
| 2014/0358066 A1 | 12/2014 | Nuccitelli et al. |
| 2014/0364797 A1 | 12/2014 | Schoenbach |
| 2015/0320999 A1 | 11/2015 | Nuccitelli et al. |

OTHER PUBLICATIONS

Beebe et al., "Diverse Effects of Nanosecond Pulsed Electric Fields on Cells and Tissues," DNA and Cell Biology, 2003, vol. 22, No. 12, pp. 785-796.

Bier et al. 1999. Kinetics of Sealing for Transient Electropores in Isolated Mammalian Skeletal Muscle Cells, Bioelectromagnetics, vol. 20, pp. 194-201.

Borner et al. 1994, The detergent Triton X-100 induces a death pattern in human carcinoma cell lines that resembles cytotoxic lymphocyte-induced apoptosis. FEBS Lett. 353: pp. 129-132.

Chen, X. et al., "Apoptosis initiation and angiogenesis inhibition: melanoma targets for nanosecond pulsed electric fields," Pigment Cell Melanoma Research, Apr. 2, 2010, 23, 554-563.

Chen, X. et al., "Comparative study of nanosecond electric fields in vitro and in vivo on hepatocellular carcinoma indicate macrophage infiltration contribute to tumor ablation in vivo," PLOS.One, vol. 1, No. 9, e86421, pp. 1-7 (Jan. 2014).

(56) References Cited

OTHER PUBLICATIONS

Chen, X. et al., "Long Term Survival of Mice With Hepatocellular Carcinoma after Pulse Power Ablation with Nanosecond Pulsed Electric Fields," Technol. Cancer Res. Treat. 11, 83-93 (2012).

Cole et al. 2001, Time-domain whole-field fluorescence lifetime imaging with optical sectioning; Journal of Microscopy, vol. 203, Pt. 3, Sep. 2001, pp. 246-257.

Cossarizza et al. 2001. Chapter 21, Analysis of Mitochondria during Cell Death. In Methods in Cell Biology, vol. 63, pp. 467-486.

Craft et al. 1998, "PhLPs and PhLOPs in the phosducin family of G beta gamma binding proteins," American Chemical Society, Biochemistry 37: pp. 15758-15772.

Cubeddu et al. 2002, Time-resolved fluorescence imaging in biology and medicine; Topical Review; Institute of Physics Publishing, J. Phys.D; Appl.Phys, 35: pp. R61-R76.

Deangelis L. M., 2001, Brain Tumors. New England Journal of Medicine, v. 344: pp. 114-123.

Debruin et al., 1999, Modeling electroporation in a single cell. I. Effects offield strength and rest potential. Biophysical Journal, vol. 77, Sep. 1999: pp. 1213-1224.

Deng, J. et al., "The effects of intense submicrosecond electrical pulses on cells," Biophysical Journal, Apr. 2003, 84(4) 2709-2714.

Frank et al., 1998. High-power Pseudospark and BLT switches. IEEE Trans. Plasma Science 16 (2): pp. 317-323.

Freeman et al., 1994, Theory of electroporation of planar bilayer membranes: predictions of the aqueous area, change in capacitance, and pore-pore separation. Biophysical Journal, vol. 67, Jul. 1994: pp. 42-56.

Gabriel, B. et al, "Generation of reactive-oxygen species induced by electropermeabilization of Chinese hamster ovary cells and their consequence on cell viability," Eur. J. Biochem. 223, 25-33 (1994).

Garg, A.D. et al., "A novel pathway combining calreticulin exposure and ATP secretion in immunogenic cancer cell death," EMBO J. 31, 1062-1079 (2012).

Garg, A.D. et al., "Hypericin-based photodynamic therapy induces surface exposure of damage-associated molecular patterns like HSP70 and calreticulin," Cancer Immunol. Immunother. 61, 215-221 (2012).

Garon et al., 2007, In Vitro and In Vivo Evaluation and a Case Report of Intense Nanosecond Pulsed Electric Field as a Local Therapy for Human Malignancies. Int. J. Cancer, vol. 121, pp. 675-682.

Gilbert et al. 1997. Novel electrode designs for electrochemotherapy. Biochimica et Biophys. Acta vol. 1334, pp. 9-14.

Gotoh et al. 2002. Nitric Oxide-induced Apoptosis in RAW 264.7 Macrophages Is Mediated by Endoplasmic Reticulum Stress Pathway Involving ATF6 and CHOP. J. Biol. Chem. vol. 277, No. 14, Apr. 2002: pp. 12343-12350.

Grekhov et al. 1983. Formation of Nanosecond High-Voltage Drop Across Semiconductor Diodes with Voltage Recovery by a Drift Mechanism. Sov. Tech Phys. Lett., vol. 9, No. 4: pp. 188-189.

Grekhov et al. 2000 Physical Basis for High-Power Semiconductor Nanosecond Opening Switches. IEEE Transactions on Plasma Science, vol. 28: pp. 1540-1544.

Grekhov et al. 2005. Nanosecond Semiconductor Diodes for Pulsed Power Switching. Physics-Uspekhi, vol. 48, No. 7: pp. 703-712.

Gundersen et al. 2004. Nanosecond Pulse Generator Using a Fast Recovery Diode. IEEE 26.sup.th Power Modulator Conference, pp. 603-606.

Hemker et al. 1999. Development of a parallel code for modeling plasma based accelerators. IEEE Particle Accelerator Conference 5: pp. 3672-3674.

Hennings et al. 1985. Induction of papillomas with a high probability of conversion to malignancy. Carcinogenesis vol. 6, pp. 1607-1610.

Hennings et al. 1986. Malignant conversion and metastasis of mouse skin tumors: a comparison of SENCAR and CD-1 mice. Environmental health perspectives, vol. 68, pp. 69-74.

Hewlett Packard. 1984. Application Note 918, Pulse and Waveform Generation with Step Recovery Diodes. Oct. 1984. 22 pages.

International Application No. PCT/US09/45073, International Search Report dated Dec. 18, 2009, 2 pages.

Joshi et al. 2000. Electroporation dynamics in biological cells subjected to ultrafast electrical pulses: A numerical simulation study, Physical Review E, vol. 62, Jul. 2000: pp. 1025-1033.

Kirkman et al. 1986. Low pressure, light initiated, glow discharge switch for high power applications. Appl. Phys. Lett., vol. 49, Sep. 1986: pp. 494-495.

Kotnik et al. 2000. Theoretical evaluation of the distributed power dissipation in biological cells exposed to electric fields, Bioelectromagnetics, vol. 21: pp. 385-394.

Kotov et al., A Novel Nanosecond Semiconductor Opening Switch for Megavolt Repetitive Pulsed Power Technology: Experiment and Applications. In Proceedings of the 9th Int. IEEE Pulsed Power Conference, Albuquerque, NM, 1993, pp. 134-139.

Kroemer, G. et al., "Classification of cell death: recommendations of the Nomenclature Committee on Cell Death 2009," Cell Death Differ. Jan, 2009; 16(1): 3-11. Published online Oct. 10, 2008. doi: 10.1038/cdd.2008.150.

Krysko, D.V. et al., "Clearance of apoptotic and necrotic cells and its immunological consequences," Apoptosis, 11, 1709-1726 (2006).

Krysko, D.V. et al., "Immunogenic cell death and DAMPs in cancer therapy," Nature Reviews | Cancer, 12, 860-875 (Dec. 2012).

Kudo, M., "Hepatocellular carcinoma in 2011 and beyond: from the pathogenesis to molecular targeted therapy," Oncology. 81 Suppl 1:1-10. Epub@2011 Dec. 22, 1-10 (2011).

Li et al. 2002. Retinoic acid upregulates cone arrestin expression in retinoblastoma cells through a Cis element in the distal promoter region. Invest Ophthalmol Vis Sci., vol. 43, No. 5, May 2002: pp. 1375-1383.

Li et al. 2003. Gene expression networks underlying retinoic acid-induced differentiation of human retinoblastoma Cells Invest Ophthalmology & Vision Science, vol. 44, No. 3, Mar. 2003: pp. 996-1007.

Long, G. et al., "Targeted tissue ablation with nanosecond pulses," IEEE Trans. Biomed. Eng. 58, 2161-2167 (2011).

Lucas, M.L. et al., "IL-12 Gene therapy using an electrically mediated nonviral approach reduces metastatic growth of melanoma," DNA and Cell Biology, 2003, 22(12) 755-763.

Lyubutin et al. 1997. Repetitive Nanosecond All-Solid-State Pulsers Based on SOS Diodes. In IEEE 11th International Pulsed Power Conference, Baltimore, MD: pp. 992-998.

Marcu et al. 1999. Photobleaching of arterial fluorescent compounds: characterization of elastin, collagen, and cholesterol time-resolved spectra during prolonged ultraviolet irradiation, Photochem. Photobiol., vol. 69, No. 6: pp. 713-721.

Marszalek et al. 1990. Schwan equation and transmembrane potential induced by alternating electric field, Biophysical Journal, vol. 58, Oct. 1990: pp. 1053-1058.

Maytin et al. 2001. Stress-Inducible Transcription Factor CHOP/gadd153 Induces Apoptosis in Mammalian Cells via p38 Kinase-Dependent and -Independent Mechanisms. Exp. Cell Res., vol. 267: pp. 193-204.

Moll et al. 1969. Physical Modeling of the Step Recovery Diode for Pulse and Harmonic Generation Circuits. In Proceedings of the IEEE, vol. 57, No. 7, Jul. 1969: pp. 1250-1259.

Nuccitelli, R. et al., "Nanoelectroablation of human pancreatic carcinoma in a murine xenograft model without recurrence," Int. J. Cancer 132, 1933-1939 (Apr. 15, 2013).

Nuccitelli, R. et al., "Nanoelectroablation therapy for murine basal cell carcinoma," Biochem. Biophys. Res. Commun. 424, 446-450 (2012).

Nuccitelli, R. et al., "Nanosecond pulsed electric field stimulation of reactive oxygen species in human pancreatic cancer cells is Ca2+-dependent," Biochem. Biophys. Res. Commun. 435, 580-585. (Jun. 14, 2013).

Nuccitelli, R. et al., "Nanosecond pulsed electric fields cause melanomas to self-destruct," Biochem. Biophys. Res. Commun. 343, 351-360 (2006).

Nuccitelli, R. et al., "Non-thermal nanoelectroablation of UV-induced murine melanomas stimulates an immune response," Pigment Cell Melanoma Res., 25:618-629 (2012).

(56) References Cited

OTHER PUBLICATIONS

Obeid, M. et al., "Calreticulin exposure dictates the immunogenicity of cancer cell death," Nat. Med. 13, 54-61 (Jan. 2007).

Pakhomova, O.N. et al., "Oxidative effects of nanosecond pulsed electric field exposure in cells and cell-free media," Arch. Biochem. Biophys. 527, 55-64 (2012).

Pogue et al. 2001. In Vivo NADH Fluorescence Monitoring as an Assay for Cellular Damage in Photodynamic Therapy; Photochemistry and Photobiology, vol. 74, No. 6, Oct. 2001: pp. 817-824.

Polevaya et al. 1999. Time domain dielectric spectroscopy study of human cells. II. Normal and malignant white blood cells. Biochim. Biophys. Acta., vol. 1419: pp. 257-271.

Ren et al., "An apoptosis targeted stimulus with nanosecond pulsed electric fields (nsPEFs) in E4 squamous cell carcinoma," Apoptosis, 2011, vol. 16, pp. 382-393.

Rukin, S.N. 1999. High-Power Nanosecond Pulse Generators Based on Semiconductor Opening Switches (Review). Instruments and Experimental Techniques, vol. 42, No. 4: pp. 439-467.

Sanders et al. 2008. Broadband Power Measurement of High-Voltage, Nanosecond Electric Pulses for Biomedical Applications. IEEE International Power Modulator Conference, Las Vegas, NV, 2008, pp. 350-353.

Schoenbach et al. 1997. The Effect of Pulsed Electric Fields on Biological Cells: Experiments and Applications, IEEE Transactions on Plasma Science, vol. 25, Apr. 1997: pp. 284-292.

Schoenbach, K.H., "Bioelectric effect of intense nanosecond pulses in Advanced Electroporation Techniques in Biology and Medicine," Eds. Pakhomov, A.G., Miklavcic, D. & Markov,M.S., 19-50, Taylor and Francis Group, Boca Raton (2010).

Slaga, T. J. 1986. SENCAR mouse skin tumorigenesis model versus other strains and stocks of mice. Environmental health perspectives, vol. 68, pp. 27-32.

Sylvester et al., "Effects of ultra-wideband electromagnetic pulses on pre-neoplastic mammary epithelial cell proliferation," Cell Prolif., 2005, vol. 38, pp. 153-163.

Tang et al. 2007. Diode Opening Switch Based Nanosecond High Voltage Pulse Generators for Biological and Medical Applications. IEEE Transactions on Dielectrics and Electrical Insulation, vol. 14, No. 4, pp. 878-883.

Vernier, P.T. et al., "Calcium bursts induced by nanosecond electric pulses," Biochem. Biophys. Res. Commun. 310, 286-295 (2003).

Wakita et al. 1995. Some Characteristics of the Fluorescence Lifetime of Reduced Pyridine Nucleotides in Isolated Mitochondria, Isolated Hepatocytes, and Perfused Rat Liver In Situ. J. Biochem., vol. 118: pp. 1151-1160.

Wang et al. 2005. Solid-State High Voltage Nanosecond Pulse Generator. IEEE Pulsed Power Conference, pp. 1199-1202.

Watanabe et al. 2002. Feasibility and limitations of the rat glioma model by C6 gliomas implanted—at the subcutaneous region. Neural. Res., vol. 24, No. 5, Jul. 2002: pp. 485-490.

Weaver et al. 1996. Theory of Electroporation: A Review. Bioelectrochemistry and Bioenergetics, vol. 41: pp. 135-160.

Webb et al. 2002. A wide-field time-domain fluorescence lifetime imaging microscope with optical sectioning. Review of Scientific Instruments, vol. 73, No. 4, Apr. 2002: pp. 1898-1907.

Weiss et al. 1984. The Role of T3 surface molecules in the activation of human T cells: a two-stimulus requirement for IL 2 production reflects events occurring at a pre-translational level. The Journal Immunology, vol. 133, No. 1, Jul. 1984: pp. 123-128.

White, J.A. et al., "Stimulation of capacitative calcium entry in HL-60 cells by nanosecond pulsed electric fields," J. Biol. Chem. 279, 22964-22972 (2004).

Yin et al., "Cutaneous Papilloma and Squamous Cell Carcinoma Therapy Utilizing Nanosecond Pulsed Electric Fields (nsPEF)", 2012, PLoS One vol. 7, No. 8, pp. e43891-e43891.

Yin et al., "Nanosecond pulsed electric field (nsPEF) treatment for hepatocellular carcinoma: A novel locoregional ablation decreasing lung metastasis," Cancer Letters, 346:285-291 (2014).

Zhu et al. 2000. The carboxyl terminal domain of phosducin functions as a transcriptional activator. Biochemical and Biophysical Research Communications, vol. 270: pp. 504-509.

Zhu et al. 2002. Mouse Cone Arrestin Gene Characterization: Promoter Targets Expression to Cone Photoreceptors. FEBS Letters, vol. 425: pp. 116-122.

\* cited by examiner

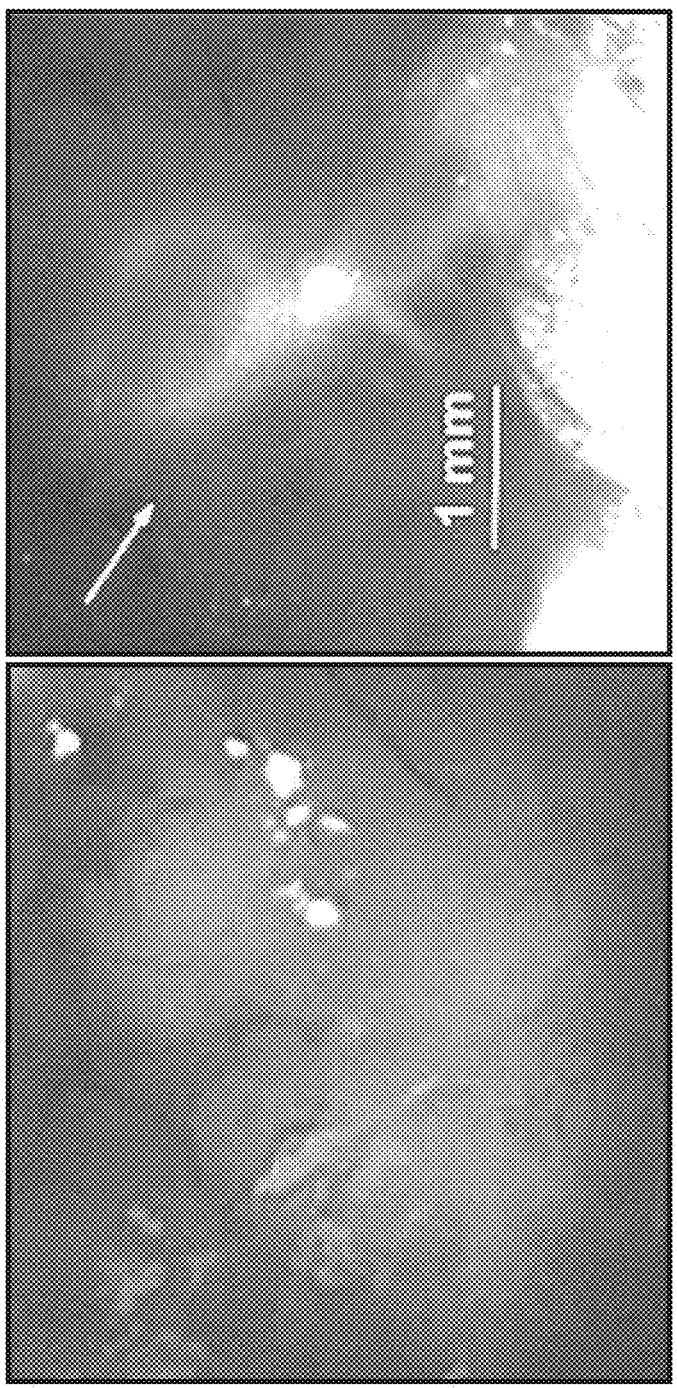

METHODS AND DEVICES FOR STIMULATING AN IMMUNE RESPONSE USING NANOSECOND PULSED ELECTRIC FIELDS

CROSS-REFERENCES TO RELATED APPLICATIONS

This application is a continuation application of co-pending U.S. application Ser. No. 15/873,810, filed Jan. 17, 2018, which is a continuation application of U.S. application Ser. No. 15/484,550, filed Apr. 11, 2017, which is a divisional application of U.S. application Ser. No. 14/805,828, filed Jul. 22, 2015 (issued as U.S. Pat. No. 9,656,066), which is a divisional application of U.S. application Ser. No. 14/287,957, filed May 27, 2014 (issued as U.S. Pat. No. 9,101,764), which claims the benefit of U.S. Provisional Application No. 61/830,564, filed Jun. 3, 2013, which are hereby incorporated by reference in their entireties for all purposes.

STATEMENT AS TO RIGHTS TO INVENTIONS MADE UNDER FEDERALLY SPONSORED RESEARCH AND DEVELOPMENT

This invention was made with government support under award numbers R01CA125722 and R44CA150484 awarded by the National Institutes of Health (NIH). The government has certain rights in the invention.

FIELD

The present application generally relates to surgical devices and methods of use, specifically those involving nanosecond pulsed electric fields (nsPEF).

BACKGROUND

Description of the Related Art

Melanoma affecting the skin is one of the top six cancers in the United States, and its rate is rising in some populations. Ultraviolet radiation from sun exposure is a leading cause of such skin cancer. Cutaneous melanoma causes a skin tumor or other lesion, which is normally treated by surgical removal.

Surgical excision of a tumor can result in an infection and leave a scar. Furthermore, if there are more tumors, every cancerous tumor should be identified and individually excised by a surgeon. This can be time consuming and expensive, not to mention uncomfortable for patients.

Cancerous tumors that are internal to a patient may be especially difficult to remove, let alone detect and treat. Many patients' lives are turned upside down by the discovery of cancer in their bodies, sometimes which have formed relatively large tumors before being detected.

A "nanosecond pulsed electric field," sometimes abbreviated as nsPEF, includes an electric field with a pulse width of between 0.1 nanoseconds (ns) and 1000 nanoseconds, or as otherwise known in the art. It is sometimes referred to as sub-microsecond pulsed electric field. NsPEFs often have high peak voltages, such as 10 kilovolts per centimeter (kV/cm), 20 kV/cm, to 500 kV/cm. Treatment of biological cells with nsPEF often uses a multitude of periodic pulses at a frequency ranging from 0.1 per second (Hz) to 10,000 Hz.

NsPEFs have been found to trigger both necrosis and apoptosis in cancerous tumors. Selective treatment of such tumors with nsPEFs can induce apoptosis within the tumor cells without substantially affecting normal cells in the surrounding tissue due to its non-thermal nature.

An example of nsPEF applied to biological cells is shown and described in U.S. Pat. No. 6,326,177 (to Schoenbach et al.), which is incorporated herein by reference in its entirety for all purposes.

The use of nsPEF for the treatment of tumors is a relatively new field. There exists a need in the art for the safe and effective treatment of cancer in human subjects.

BRIEF SUMMARY

Generally, stimulating an immune response of a human being or other subject using nanosecond pulsed electric field (nsPEF) treatments of a tumor to trigger immunogenic apoptosis in the tumor, and verifying that the immune response in the subject has been stimulated, is described. Based on a measurement of the immune response (or lack thereof), a further nsPEF treatment on the same or another tumor can be implemented. Electrical characteristics of nsPEF treatments can be based on the size and type of tumor, as well as the degree of tumor sensitivity to nsPEF and/or a quantity of tumors in the subject.

Sufficient treatment of a cancerous tumor by nsPEF can cause the expression of calreticulin (CRT) on the external surface membranes of its tumor cells. Calreticulin expression may be optimized to trigger the immune response against the underlying cancer. CD47 (cluster of differentiation 47)-blocking antibodies can be injected into the subject in conjunction with nsPEF treatment of a tumor as a combination therapy.

Not only can the triggered immune response attack the nsPEF-treated tumor, but it can also attack like-cancer cells in other tumors throughout the subject's body where a cancer has metastasized. Therefore, not every tumor in the body must be individually subject to nsPEF treatments. Instead, a readily accessible, electrode-compatible tumor may be treated, and then other tumors can be monitored for shrinkage.

Metastasized cancer can also be treated by extracting circulating tumor cells (CTCs) from the subject's bloodstream, subjecting them to nsPEF sufficient to cause calreticulin expression, and then reinjecting them into the patient's bloodstream. In some cases, a tumor may be removed from a patient, treated by nsPEF sufficient to cause calreticulin expression, and then reimplanted back into a patient's body. The reinjected CTCs or reimplanted tumor can then trigger an immune response against the cancer.

Some embodiments of the present invention are related to a method for stimulating an immune response to a disease in a subject. The method includes positioning a set of electrodes in proximity to a tumor of a disease of a subject, applying, using the electrodes, sub-microsecond pulsed electric fields to the tumor sufficient to cause the tumor to express calreticulin on surface membranes of tumor cells of the tumor, and then measuring an immune response biomarker in a sample of the subject in order to confirm a stimulation of an immune response of the subject against the disease.

The method can be performed on human subjects as well as other mammal and animal subjects. The disease can be cancerous or noncancerous.

The method can include further applying of sub-microsecond pulsed electric fields sufficient to stimulate immunogenic apoptosis in the tumor, and it can expressly include detecting calreticulin on surface membranes of the tumor cells after the applying.

The method can include introducing CD47-blocking antibodies into the subject, the CD47-blocking antibodies neutralizing CD47 on the surface membranes of the tumor cells whilst the calreticulin is expressed on the surface membranes. Introducing of CD47-blocking antibodies can occur before the positioning or the applying of sub-microsecond pulsed electric fields.

The method can include introducing injecting doxorubicin, CTLA-4 (cytotoxic T-lymphocyte antigen 4)-blocking antibodies, and/or PD-1 (programmed death 1)-blocking antibodies into the subject before the applying.

The measuring of the immune response biomarker can include measuring a concentration or level of white blood cells in the sample, such as CD4+ or CD8+T lymphocytes. Measuring the immune response biomarker can include measuring a concentration or level in the sample of a member selected from a group consisting of white blood cells, inflammatory cytokines, C-reactive proteins, and antibodies of cancer cell markers. The method can further include gauging the immune response biomarker in a sample of the subject before the applying, and comparing results of the gauging of the immune response biomarker and results of the measuring of the immune response biomarker in order to confirm the stimulation of the immune response of the subject.

The method can include administering an immune booster to the subject within fourteen days of the applying. It can also include preventing, averting, or forestalling chemotherapy treatment within one month after the applying.

The method can include monitoring the immune response biomarker over time in samples from the subject, perhaps measuring the immune response biomarker between fourteen to twenty-eight days after the applying. One can treat the tumor again based on the monitoring by positioning a set of electrodes in proximity to the tumor of the subject, and applying nanosecond pulsed electric fields to the tumor sufficient to cause the tumor to express calreticulin on surface membranes of tumor cells of the tumor and sufficient to stimulate apoptosis in the tumor. The method can include treating a second tumor in the subject, based on the monitoring, by positioning a set of electrodes in proximity to the second tumor of the subject, and applying nanosecond pulsed electric fields to the second tumor sufficient to cause the tumor to express calreticulin on surface membranes of tumor cells of the second tumor and sufficient to stimulate apoptosis in the second tumor.

The sub-microsecond pulsed electric fields can have pulse lengths of between 0.1 and 1000 nanoseconds. The sub-microsecond pulsed electric fields can have pulse lengths of between 10 and 900 nanoseconds. The sub-microsecond pulsed electric fields can have pulse lengths of about 100 nanoseconds. The sub-microsecond pulsed electric fields can have pulse amplitudes of at least 20 kilovolts per centimeter.

The method can include determining a size of the tumor, determining a type of the tumor, and applying a number of pulses greater than 50 based on the determined size and type of the tumor. The method can include calculating a target treatment energy based on the determined size and type of the tumor, and selecting a number of pulses greater than 50, an amplitude of at least 20 kilovolts per centimeter, or a pulse length between 0.1 and 1000 nanoseconds for the nanosecond pulsed electric fields based on the calculated target treatment energy.

A machine-readable tangible storage medium embodying information indicative of instructions for causing one or more machines to perform the calculating and selecting operations. The method can further include selecting a repetition frequency of the nanosecond pulsed electric fields based on the determined size and type of the tumor.

The method can include quantifying a strength (e.g., a resistance of a tumor in response to a certain treatment, quantifying nsPEF pulse parameters required to cause apoptosis in the tumor) of tumor cells of the tumor, and applying a number of pulses greater than 50 based on the quantifying. The electrodes can include a pair of electrodes, and the positioning includes positioning one of the pair of electrodes on one side of the tumor and the other of the pair of electrodes on an opposing side of the tumor, thereby causing the electric fields to pass through the tumor.

The electrodes can include configurations selected from the group consisting of parallel plate electrodes, hemicircular electrodes, six-pole dual electrodes, and two- to fourteen-needle electrodes arranged in two parallel linear arrays.

Some embodiments are related to a method for stimulating an immune response to a tumor in a subject. The method includes gauging an immune response biomarker in a sample of a subject, identifying a size and a type of a tumor in the subject, calculating a target treatment energy based on the size and type of the tumor, selecting a number of pulses greater than 50, an amplitude of at least 20 kilovolts per centimeter, and/or a pulse length of between 0.1 and 1000 nanoseconds for sub-microsecond pulsed electric fields based on the calculated target treatment energy, flanking at least one pair of electrodes in or around the tumor or a portion thereof, applying to the tumor, using the at least one pair of electrodes, sub-microsecond pulsed electric fields having the selected number of pulses, selected amplitude, or selected pulse length, and then waiting at least seven days, and then measuring the immune response biomarker in a sample from the subject, comparing the measured and gauged immune response biomarkers, adjusting the target treatment energy based on the comparison, determining a number of pulses greater than 50, an amplitude of at least 20 kilovolts per centimeter, and/or a pulse length of between 0.1 and 1000 nanoseconds for nanosecond pulsed electric fields based on the adjusted target treatment energy; and treating the tumor again by flanking at least one pair of electrodes around the tumor, and applying to the tumor sub-microsecond pulsed electric fields based on the determined number of pulses, determined amplitude, or determined pulse length.

The method can be performed on human subjects as well as other mammal and animal subjects. The disease can be cancerous or noncancerous.

Some embodiments are related to a method of reducing metastasis of a disease in a subject. The method includes determining locations for multiple tumors in a subject, measuring a size of each tumor, selecting one of multiple tumors based on an accessibility of the locations and measured sizes of the tumors, and applying, using electrodes, sub-microsecond pulsed electric fields to the selected tumor sufficient to cause the tumor to express calreticulin on surface membranes of tumor cells of the selected tumor.

The method can be performed on human subjects as well as other mammal and animal subjects. The disease can be cancerous or noncancerous.

The accessibility of each tumor can be determined by identifying pathways to opposed sides of the respective tumor that can be contacted by electrodes through pierceable paths in the subject. A tumor can be selected based on the selected tumor being adjacent to a stomach wall.

Some embodiments are related to a method of reducing metastasis of a cancerous disease in a subject. The method can include isolating circulating tumor cells (CTCs) from a bloodstream of a subject, amassing the tumor cells into an in vitro mass of tumor cells, passing sub-microsecond pulsed electric fields through the in vitro mass of tumor cells, thereby treating the tumor cells, and then introducing the treated tumor cells into the subject.

The method can be performed on human subjects as well as other mammal and animal subjects. The disease can be cancerous or noncancerous.

The passing of sub-microsecond pulsed electric fields can be sufficient to cause at least some of the tumor cells of the in vitro mass to express calreticulin on surface membranes of the at least some of the tumor cells. The method can include introducing CD47-blocking antibodies into the subject. The method can optionally include contacting an electrode to the in vitro mass.

Some embodiments are related to using a biopsy from a tumor to treat a cancerous disease in a subject. The method includes extracting a sample of cells from a tumor of a subject, passing sub-microsecond pulsed electric fields through the extracted sample of tumor cells sufficient to stimulate apoptosis in the tumor cells, thereby treating the tumor cells, confirming that the tumor cells of the sample have initiated apoptosis and are no longer capable of dividing, and then introducing the treated tumor cells into the subject. The removal of tumor cells can be performed by fine needle aspiration or other suitable process.

The method can be performed on human subjects as well as other mammal and animal subjects. The disease can be cancerous or noncancerous.

Yet other embodiments relate to systems and machine-readable tangible storage media that employ or store instructions for the methods described above.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 28A is an image of a primary liver tumor one week after injection.

FIG. 28B is an image of a secondary liver tumor three weeks after nsPEF treatment of the first tumor (in FIG. 28A) in accordance with an embodiment.

DETAILED DESCRIPTION

Figure 1:
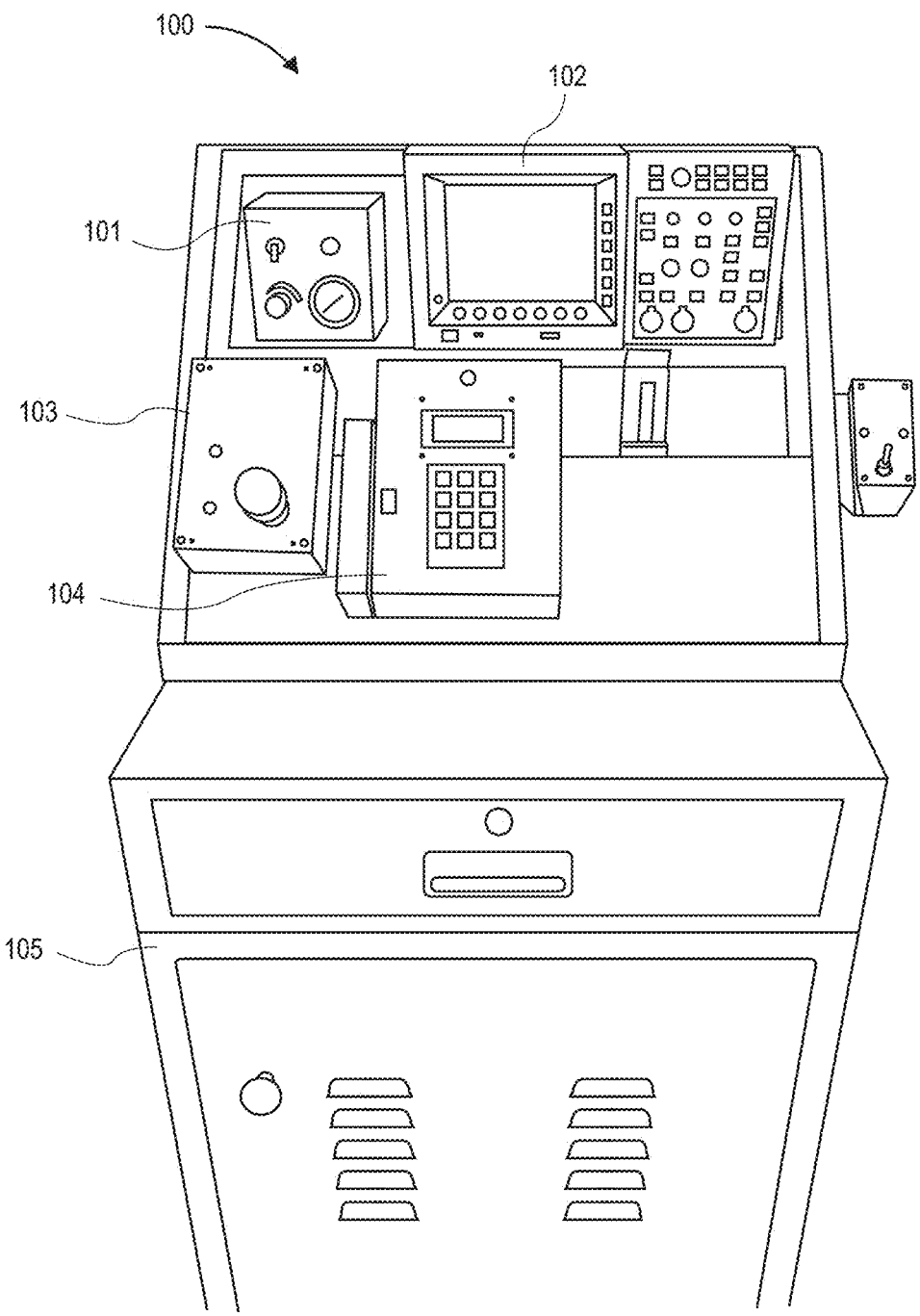
FIG. 1 illustrates a nanosecond pulse generator apparatus in accordance with an embodiment.

It has been shown that nsPEF treatments can be used to cause cancerous tumors to express calreticulin on their cell surface membranes, which may be sufficient to stimulate an immune response that inhibits subsequent tumor growth and/or mitigate metastasis. An nsPEF treatment can be sufficient to stimulate immunogenic apoptosis in the primary tumor that is actually subject to the nsPEF pulses, while the immune response can attack secondary tumors that were not so directly treated.

A "tumor" includes any neoplasm or abnormal, unwanted growth of tissue on or within a subject, or as otherwise known in the art. A tumor can include a collection of one or more cells exhibiting abnormal growth. There are many types of tumors. A malignant tumor is cancerous, a pre-malignant tumor is precancerous, and a benign tumor is noncancerous. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus.

A "disease" includes any abnormal condition in or on a subject that is associated with abnormal, uncontrolled growths of tissue, including those that are cancerous, pre-cancerous, and benign, or other diseases as known in the art.

"Apoptosis" of a tumor or cell includes an orderly, programmed cell death, or as otherwise known in the art.

"Immunogenic apoptosis" of a tumor or cell includes a programmed cell death that is followed by an immune system response, or as otherwise known in the art. The immune system response is thought to be engaged when the apoptotic cells express calreticulin or another antigen on their surfaces, which stimulates dendritic cells to engulf, consume, or otherwise commit phagocytosis of the targeted cells leading to the consequent activation of a specific T cell response against the target tumor or cell.

Pulse lengths of between 10 and 900 nanoseconds for nsPEF have been particularly studied to be effective in stimulating an immune response. Pulse lengths of about 100 nanoseconds are of particular interest in that they are long enough to carry sufficient energy to be effective at low pulse numbers but short enough to be effective in the manner desired.

A time of "about" a certain number of nanoseconds includes times within a tolerance of ±1%, 2%, 3%, 4%, 5%, 7.5%, 10%, 15%, 20%, 25% or other percentages, or fixed tolerances, such as ±0.1, ±0.2, ±0.3, ±0.4, ±0.5, ±0.7, ±1.0, ±2.0, ±3.0, ±4.0±5.0, ±7.0, ±10, ±15, ±20, ±25, ±30, ±40, ±50, ±75 ns, or other tolerances as acceptable in the art in conformance with the effectivity of the time period.

Immune system biomarkers can be measured before and/or after nsPEF treatment in order to confirm that the immune response has been triggered in a patient. Further, nsPEF treatment can be paired with CD47-blocking antibody treatment to better train CD8+ T cells (i.e., cytotoxic T cells) for attacking the cancer.

U.S. Patent Application Publication No. US 2011/0288545 A1 (to Beebe et al.) discloses that mice with subdermal injections of hepatocellular carcinoma cells (HCC) developed immunity against HCC after one nsPEF treatment. This conclusion is based on the stagnation of secondary tumors of HCC, which were initiated in the mice after their first tumors had been eliminated by nsPEF. Yet, there is no disclosure in the reference of measuring immune response biomarkers. Instead it was observed that secondary tumors injected after treatment did not grow, which is an indirect indication of an immune response. The effects of nsPEF on concurrent secondary tumors (i.e., tumors that exist in the subject that are not treated with nsPEF while a primary tumor is treated with nsPEF) are not disclosed.

In an embodiment, immune response biomarkers, such as a concentration of CD4+ and/or CD8+T lymphocyte white blood cells in the bloodstream of a patient, are sampled in order to confirm stimulation of the patient's immune system. Other biomarkers include concentrations and/or levels in a sample inflammatory cytokines, C-reactive proteins, and antibodies of cancer cell markers. The biomarkers can be gauged or measured both before and after nsPEF treatment in order to determine or confirm whether, and to what extent, the subject's immune response has been stimulated.

Combination Therapies

Induction of tumor antigen-specific cytotoxic T lymphocytes often results in growth inhibition and even shrinkage of solid tumors. Presentation of tumor-derived antigens by dendritic cells (DC) might be a necessary step in the induction of an immune response to the tumor. It is thought that DCs can only acquire antigens from apoptotic cells and stimulate antigen-specific MHC class I-restricted cytotoxic T lymphocytes.

There are at least three factors that can influence DC phagocytosis of tumor cells: 1) Apoptotic death may be a requirement for antigen presentation because antigens from necrotic cells cannot enter this pathway. Moreover, a high ratio of apoptotic cells-to-DCs can also induce DC maturation and enhance the DC ability to efficiently present antigens derived from the apoptotic cells to T cells. 2) Exposure of calreticulin on the cell surface may be an "eat me" signal that stimulates phagocytosis of the tumor cells by DCs. 3) CD47 is commonly highly expressed on many tumor cells and functions as a "don't eat me" signal, inhibiting the phagocytosis by DCs. Consequently, blocking CD47 using antibodies directed to it may enhance phagocytosis and lead to a stronger immune response.

Proper nanoelectroablation can result in the activation of two of these factors for phagocytosis of the tumor cells. It triggers apoptosis and the exposure of calreticulin on the tumor cell surface. This therapy might be even more effective if it is combined with other therapies known to influence one or more of the three critical factors above. One such combination therapy is to administer by intraperitoneal (IP) injection antibodies to CD47 approximately twenty-four hours before treating with nsPEF. These antibodies can bind to tumor cell CD47 and reduce the CD47 inhibitory effect on DCs. NsPEF-stimulated calreticulin expression can then stimulate DC phagocytosis of the tumors cells so that the DCs can present tumor antigens to stimulate antigen-specific MHC class I-restricted cytotoxic T lymphocytes.

Another possible combination therapy is to pretreat the patient with chemotherapeutic drugs that have been found to stimulate the surface expression of calreticulin. Anthracyclines and oxaliplatin are important drugs used in the management of leukemia, lymphoma, sarcoma and uterine, ovarian and breast cancers. They may induce immunogenic apoptosis that is characterized by the exposure of calreticulin on the cell surface and secretion of adenosine triphosphate (ATP). Calreticulin and ATP interact with surface receptors on dendritic cells to promote engulfment of dying cells and presentation of tumor antigens. One of the most popular of the anthracyclines is doxorubicin (e.g., a ADRIAMYCIN PFS® or ADRIAMYCIN RDF® pharmaceutical preparation) because of its lower toxicity and high efficacy against solid tumors (*Cancer Res.* 71:4809, Jul. 15, 2011). Therefore, one combination therapy that can enhance the immune response is to treat patients first with doxorubicin followed by nsPEF treatment of the tumor.

Another combination therapy that can be used involves the T cells themselves. On the surface of just about every helper T cell is a protein called either CTLA-4 or CD152. The activation of this protein on the helper T cell inhibits the cytotoxic T cell attack when bound by a tumor cell. Antibodies directed against CTLA-4 have been shown to enhance the immune response to some tumor types such a melanoma. Injecting antibodies to CTLA-4 into the patient about 24 hours before treating the tumor with nsPEF may achieve an enhanced immune response.

Another member of the CTLA-4 family is the "programmed death 1" (PD-1) membrane protein. It is found on the surfaces of activated T cells, B cells, and macrophages, and it negatively regulates immune responses. A receptor for PD-1 is PD-L1, and PD-L1 is expressed on almost all murine tumor cell lines. When PD-1 binds to this receptor, normal T cell activation and expansion is inhibited. Antibodies developed against PD-1 have been found to enhance immune function, similar to antibodies against CTLA-4. Another combination therapy is to inject anti-PD-1 antibodies about twenty-four hours before treating the tumor with nsPEF.

FIG. 1 illustrates a nanosecond pulse generator apparatus in accordance with an embodiment. Pulse widths, duty cycles, and other pulse parameters are controlled by a spark gap, the critical distance of which is controlled by compressed gas, such as compressed carbon dioxide. NsPEF system 100 includes pressure readout 101, digitizing oscilloscope 102, emergency off button 103, and microcontroller interface 104, all connected to nsPEF generation system 105 within a metal-shielded cabinet.

A human operator inputs a number of pulses, amplitude, and frequency into a numeric keypad of microcontroller interface 104. In this embodiment, the pulse width is fixed. Microcontroller sends signals to a high voltage power supply (HVPS) and pressure system to control a spark gap (switch) within cabinet 105. Fiber optic cables electrically isolate the contents of the metal cabinet with nsPEF generation system 105, the high voltage circuit, from the outside. In order to further isolate the system, system 100 is battery powered instead of from a wall outlet.

Figure 2:
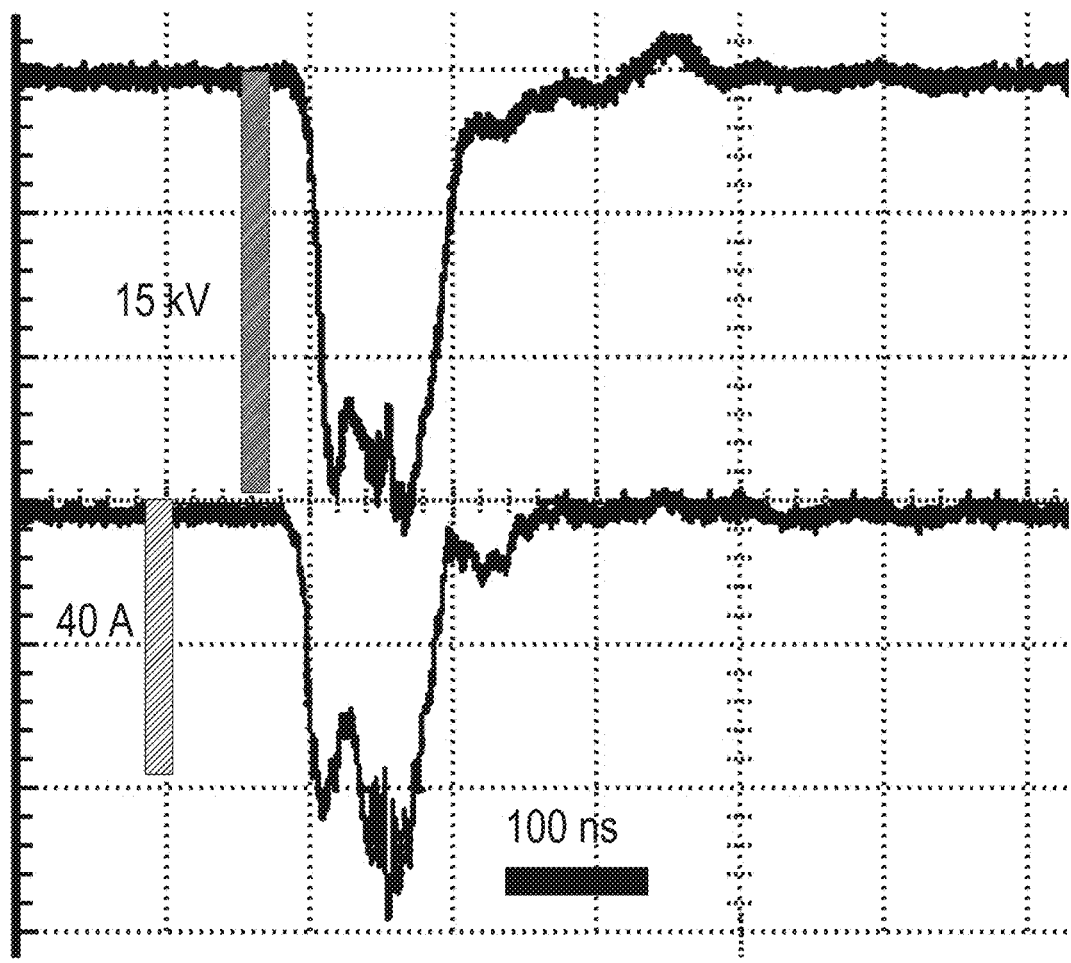
FIG. 2 illustrates oscilloscope traces of a pulse profile for both voltage and current in accordance with an embodiment.

FIG. 2 illustrates oscilloscope traces of a pulse profile for both voltage and current in accordance with an embodiment. Output from the spark gap is shown with voltage on the top of the figure and amperage on the bottom for a single pulse. The pulse has an amplitude of about 12 kV and an amperage of about 60 A, which lasts for approximately 100 ns. Thus, twelve kilovolts was applied to suction electrodes with 4 mm between the plates so that the tumors experienced 30 kV/cm, and current varied between 12 and 60 A. Given a voltage, current depends heavily on the electrode type and skin resistance.

Figure 3:
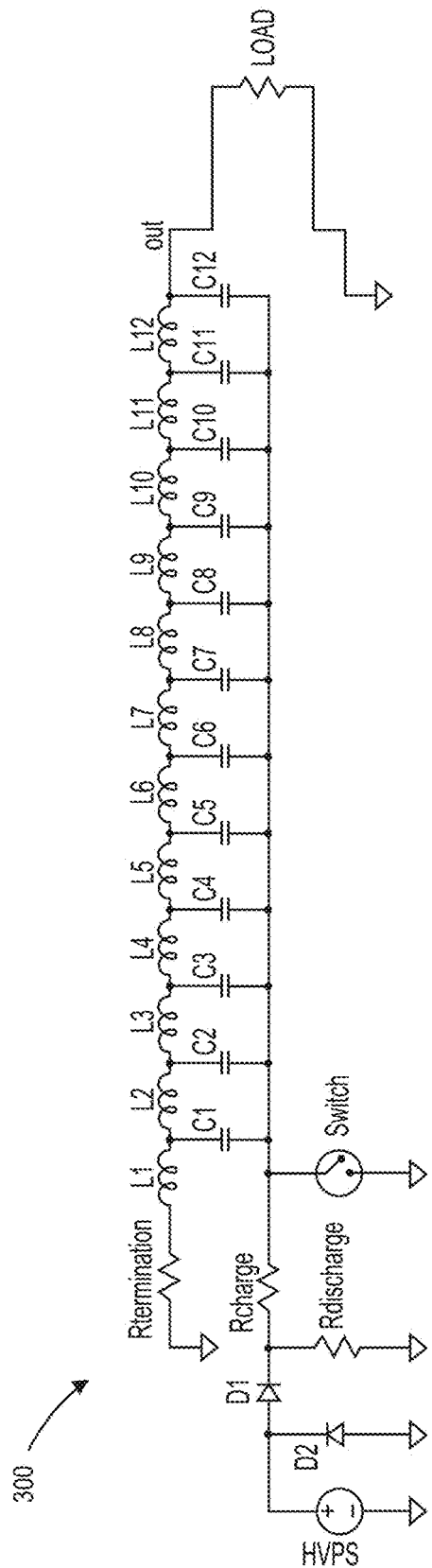
FIG. 3 is an electrical schematic of a pulse generator shown in FIG. 1.

FIG. 3 is an electrical schematic of a pulse generator inside nsPEF system 100 wired in a transmission line arrangement (see FIG. 1). High voltage circuit 300 can be entirely shielded within the cabinet of nsPEF generation system 105. High voltage circuit 300 includes a high voltage power supply HVPS, diode D2, resistor Rdischarge, and spark gap switch, all connected in parallel to ground. Between D2 and Rdischarge is diode D1, and between Rdischarge and the switch is resistor Rcharge.

The switch is directly connected to the positively-charged (+) terminals of twelve high voltage capacitors, C1 through C12. Between each capacitor at the other end (i.e., the opposite terminal) is a high-current capable inductor, L2 through L12, which are all connected to ground in series through high current-capable inductor L1 and resistor Rtermination. Output from bank of capacitors flows to a load, modeled as an ideal resistor LOAD, to ground.

To charge the capacitors, the spark gap switch is opened and the HVPS charges capacitors C1-C12. When the spark gap switch is closed, the capacitors rapidly discharge from their positive terminals through the switch to ground. Electrons from the negative terminals of the capacitors rush through inductors L1-L12 through LOAD to ground.

In an exemplary embodiment, discharging through a triggered spark gap delivers a 100-ns long pulse with a 20 ns rise time. Microcontroller interface 104 is used to trigger the spark gap at 2, 3, 4, 5, or 7 pulses per second (pps), control the voltage level of the power supply and count the pulses. The pulse counter utilizes the signal generated by a custom current sensor placed around one of the wires connected to the suction electrode so that only pulses resulting in current delivery to the tumor are counted.

Figure 4:
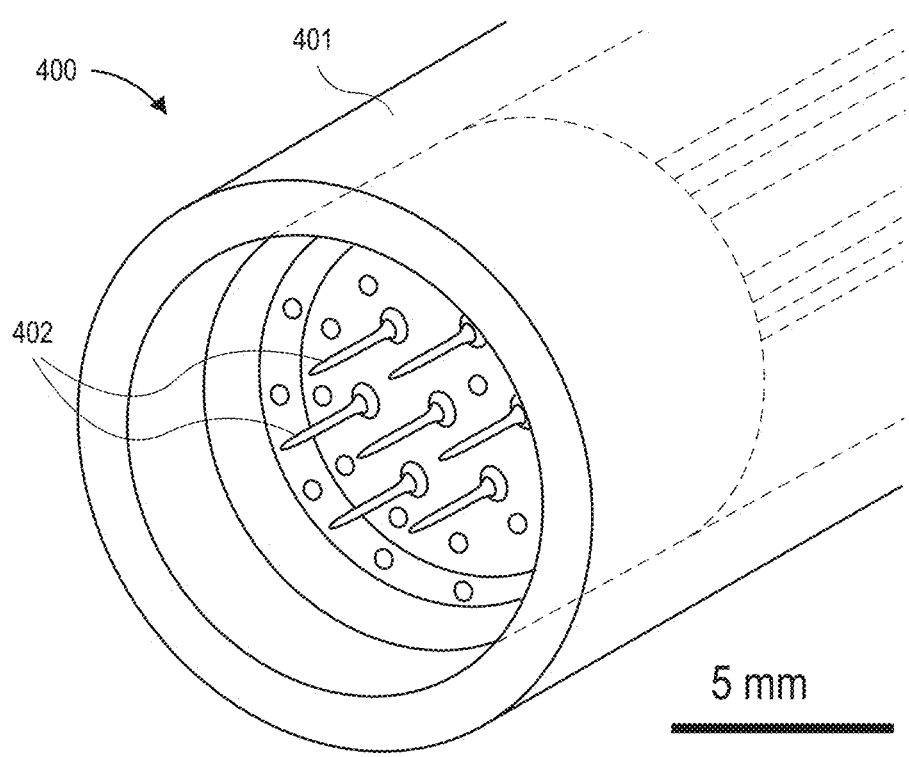
FIG. 4 illustrates a perspective view of a seven-needle electrode in accordance with an embodiment.

FIG. 4 illustrates a perspective view of a seven-needle suction electrode in accordance with an embodiment. In electrode 400, sheath 401 surrounds seven sharp electrodes 402 with an broad opening at a distal end. When the open end is placed against a tumor, air is evacuated from the resulting chamber sufficient to draw the entire tumor or a portion thereof into the chamber. The tumor is drawn so that one or more of the electrodes preferably penetrates the tumor. Sharp ends of the electrodes are configured to pierce the tumor. The center electrode is at one polarity, and the outer six electrodes are at the opposite polarity. Nanopulses electric fields can then be precisely applied to the tumor using nsPEF system 100 (see FIG. 1).

The electrodes can be opposed, one of each positive and negative pair of electrodes on one side of a tumor and the other electrode of the pair on an opposing side of the tumor. Opposing sides of a tumor can include areas outside or within a tumor, such as if a needle electrode pierces a portion of the tumor.

Figure 5A:
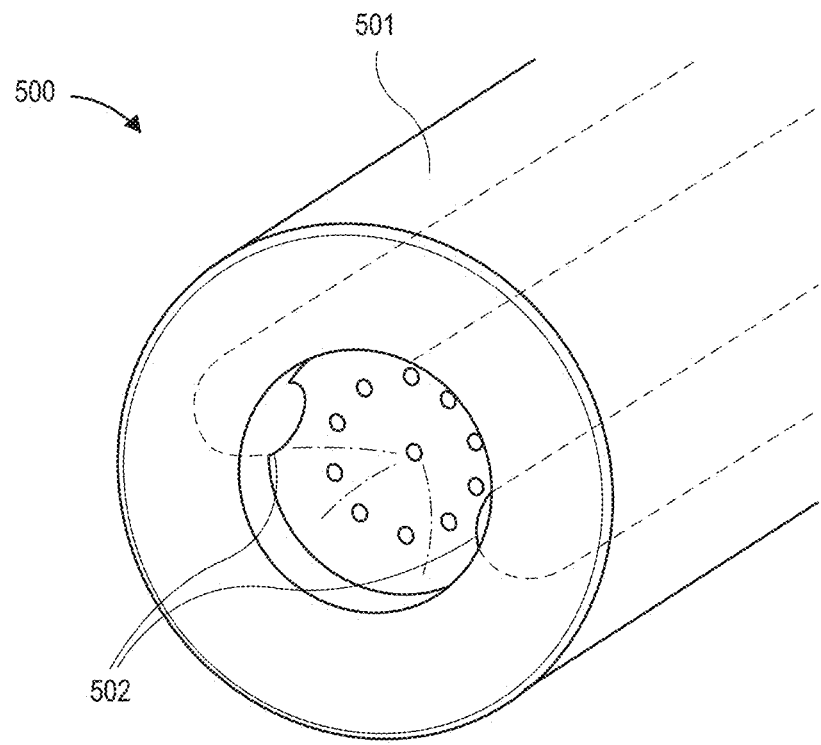
FIG. 5A illustrates a perspective view of a two-pole electrode in accordance with an embodiment.
Figure 5B:
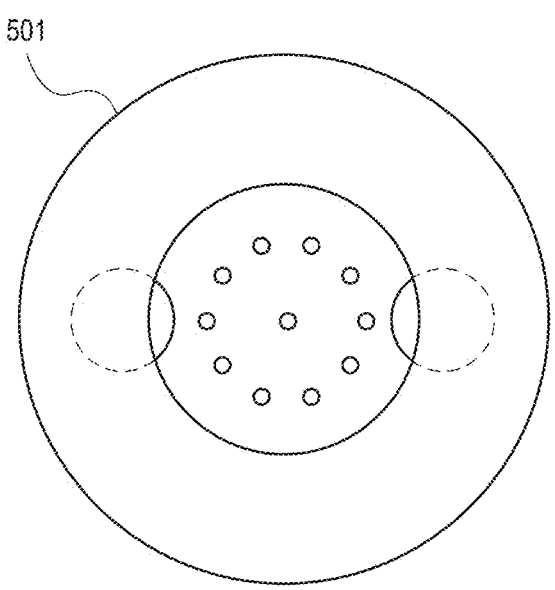
FIG. 5B illustrates an end view of the electrode of FIG. 5A.

FIGS. 5A-5B illustrate a two-pole suction electrode in accordance with an embodiment. In electrode device 500, sheath 501 surrounds two broad electrodes on opposite sides of a chamber. When air is evacuated and a tumor is pulled within the chamber, the opposing electrodes apply nsPEF pulses to the tumor.

Figure 6A:
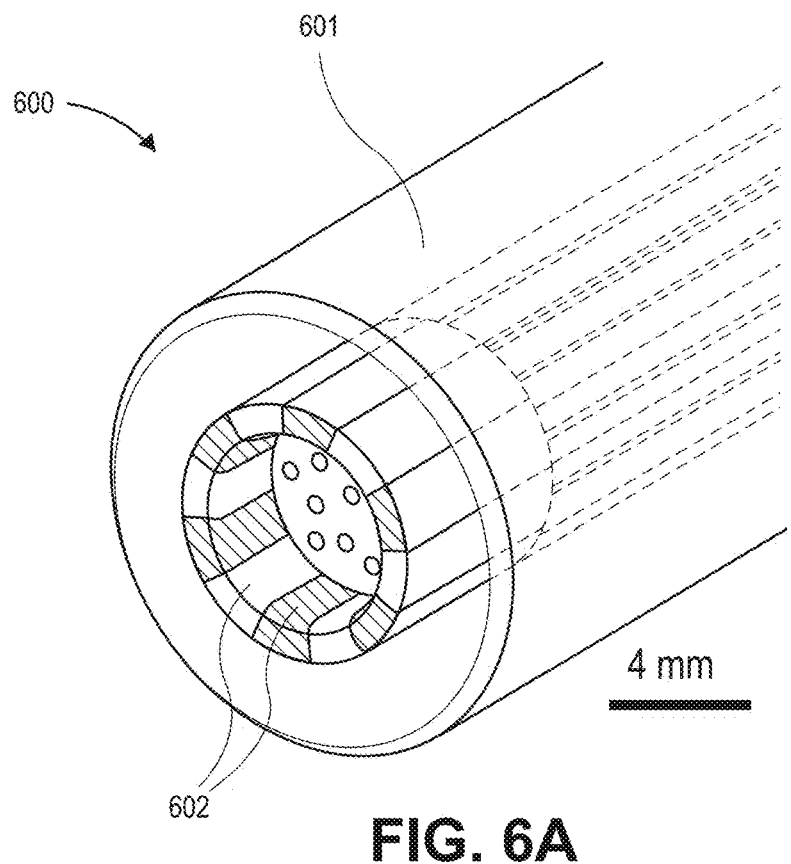
FIG. 6A illustrates a perspective view of a six-pole electrode in accordance with an embodiment.
Figure 6B:
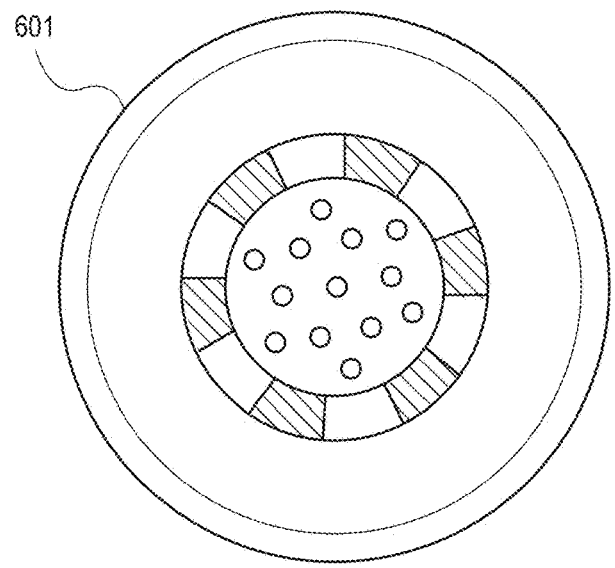
FIG. 6B illustrates an end view of the electrode of FIG. 6A.

FIGS. 6A-6B illustrate a six-pole suction electrode in accordance with an embodiment. In electrode device 600, sheath 601 surrounds six electrodes 602, which are spaced equally around the circumference of the chamber. One or more of electrodes 602 can be energized in order to effectively pulse a tumor, which is drawn inside by suction.

Figure 7A:
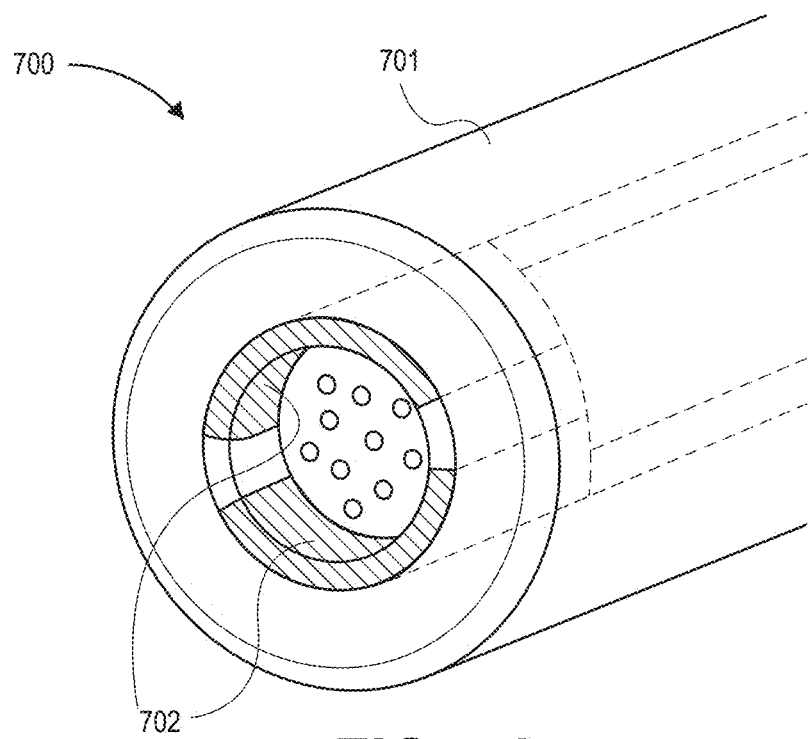
FIG. 7A illustrates a perspective view of a hemispherical electrode in accordance with an embodiment.
Figure 7B:
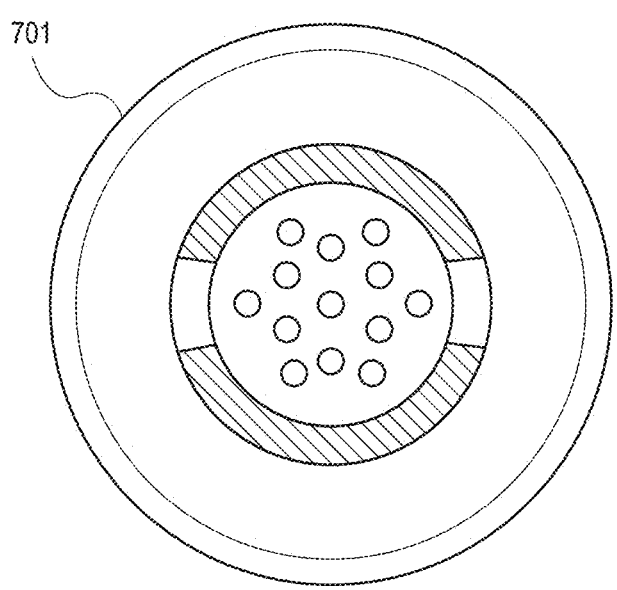
FIG. 7B illustrates an end view of the electrode of FIG. 7A.

FIGS. 7A-7B illustrate a hemispherical suction electrode in accordance with an embodiment. In electrode device 700, sheath 701 surrounds two electrodes 702 that curve around a majority of the circumference of the chamber. Relatively small gaps separate electrodes 702.

Figure 8A:
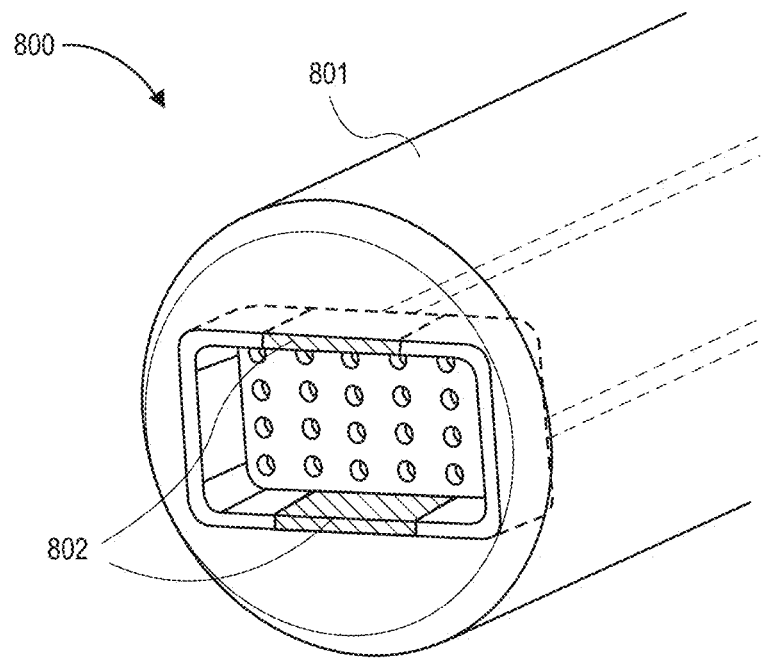
FIG. 8A illustrates a perspective view of a parallel plate electrode in accordance with an embodiment.
Figure 8B:
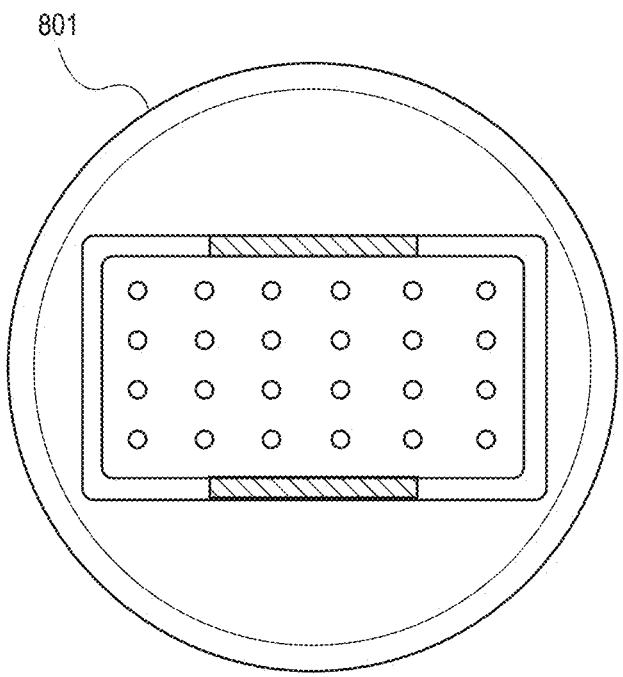
FIG. 8B illustrates an end view of the electrode of FIG. 8A.

FIGS. 8A-8B illustrate a parallel plate suction electrode in accordance with an embodiment. In electrode device 800, circular cross-section sheath 801 surrounds a rectangular chamber. Along the long sides of the rectangles, flat electrodes 802 are opposed from one another.

The nature of the electrode used mainly depends upon the shape of the tumor. Its physical size and stiffness can also be taken into account in selection of a particular electrode type.

U.S. Pat. No. 8,688,227 B2 (to Nuccitelli et al.) discloses other suction electrode-based medical instruments and systems for therapeutic electrotherapy, and it is hereby incorporated by reference.

If there are multiple tumors in a subject, a surgeon can select a single tumor to treat based on the tumors compatibility with electrodes. For example, a tumor that is adjacent to a stomach wall may be more easily accessible than one adjacent a spine or the brain. Because a nsPEF pulse is preferably applied so that the electric field transits through as much tumor mass as possible while minimizing the mass of non-tumor cells that are affected, a clear path to two opposed 'poles' of a tumor may also be a selection criterion.

A "pierceable path" is a pathway that is unobstructed by bone, nervous system conduits, vital organs, or other material that is either difficult to pierce with an electrode or more sensitive to damage than other regions of the body.

For tumors on or just underneath the skin of subject, needle electrodes can be used percutaneously. For locations deeper within a subject, a retractable electrode can fit into a gastroscope, bronchoscope, colonoscope, or other endoscope or laparoscope. For example, a tumor in a patient's colon can be accessed and treated using an electrode within a colonoscope. When moving into position within the body of the subject, the retractable electrode is in a retracted position; when in position at a tumor, the retractable electrode is deployed.

Barrett's esophagus, in which portions of tissue lining a patient's esophagus are damaged, may be treated using an electrode placed on an inflatable balloon.

Figure 9:
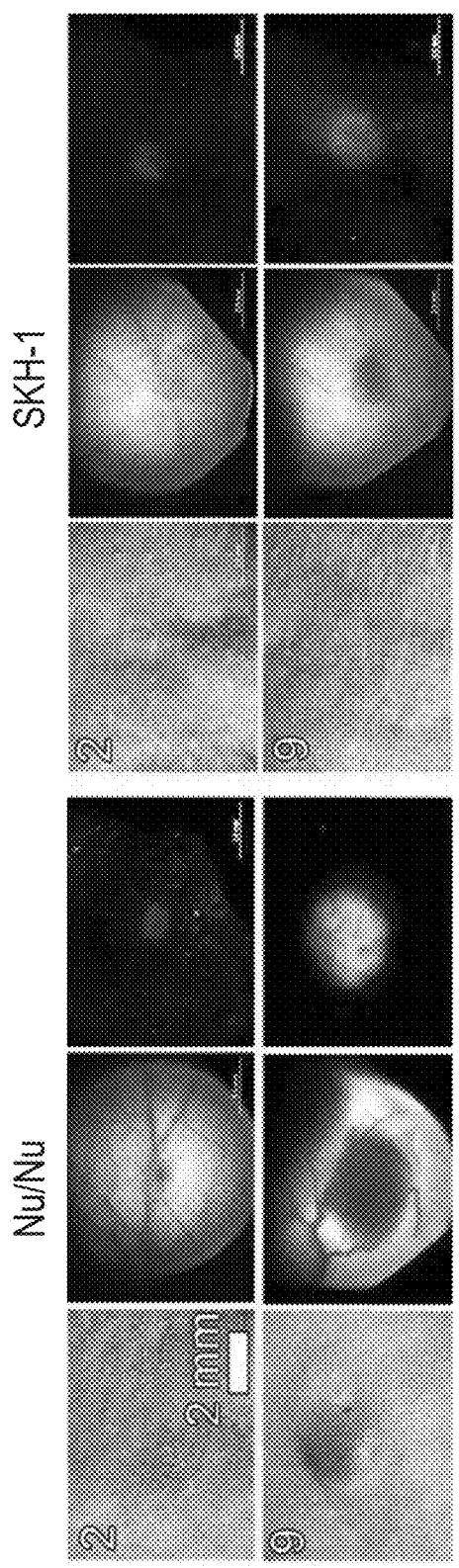
FIG. 9 includes pictures of typical growth of a first melanoma injected into immunodeficient mice (Nu/Nu) and immunocompetent mice (SKH-1).

FIG. 9 includes pictures of typical growth of a first melanoma injected into immunodeficient mice (Nu/Nu) and immunocompetent mice (SKH-1). The leftmost column shows reflected light surface views, the second column shows transilluminated views, and the third column shows fluorescent images of the Nu/Nu mice. The fourth column shows reflected light surface views, the fifth column shows transilluminated views, and the rightmost column shows fluorescent images of the SKH-1 mice. The day after injection on which the photographs were taken is indicated in the upper left of the reflected light image.

The photographs show normal (control) growth of a melanoma after 2 and 9 days. One can see that the tumor enlarges.

Figure 10:
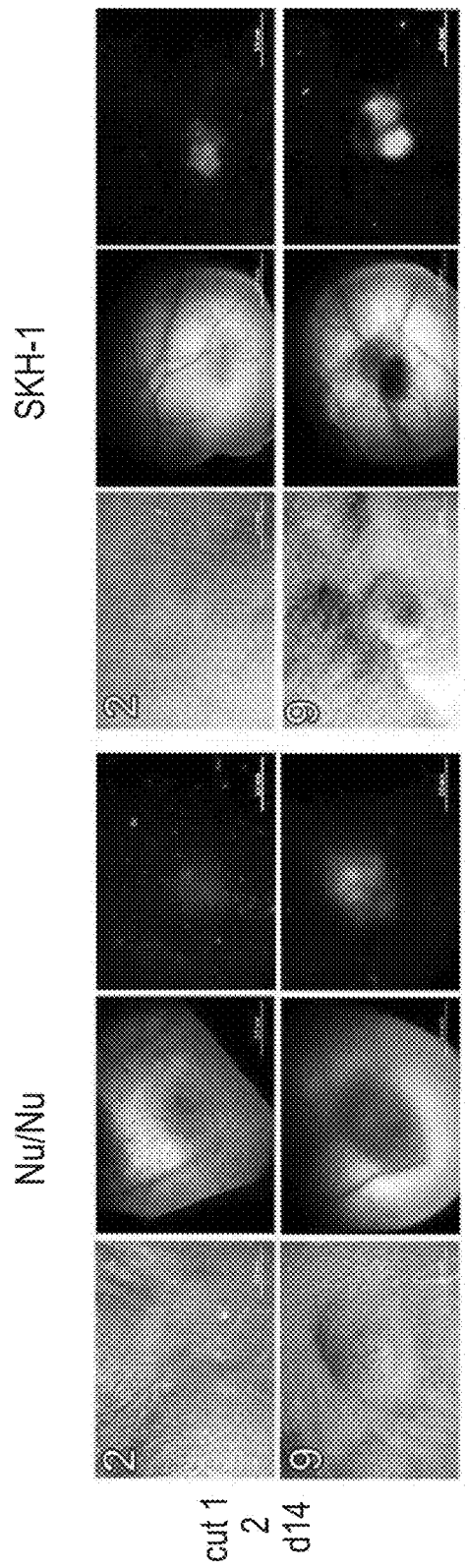
FIG. 10 includes pictures of a second tumor growing from cells injected 14 days after the first tumor was removed by surgical excision of the prior art.

FIG. 10 includes pictures of a second tumor growing from cells injected 14 days after the first tumor was removed by surgical excision of the prior art. The arrangement of pictures is the same of that as in FIG. 9.

The photographs show normal (control) growth of second tumors. One can see that the tumors grow essentially the same as the first tumors.

Figure 11:
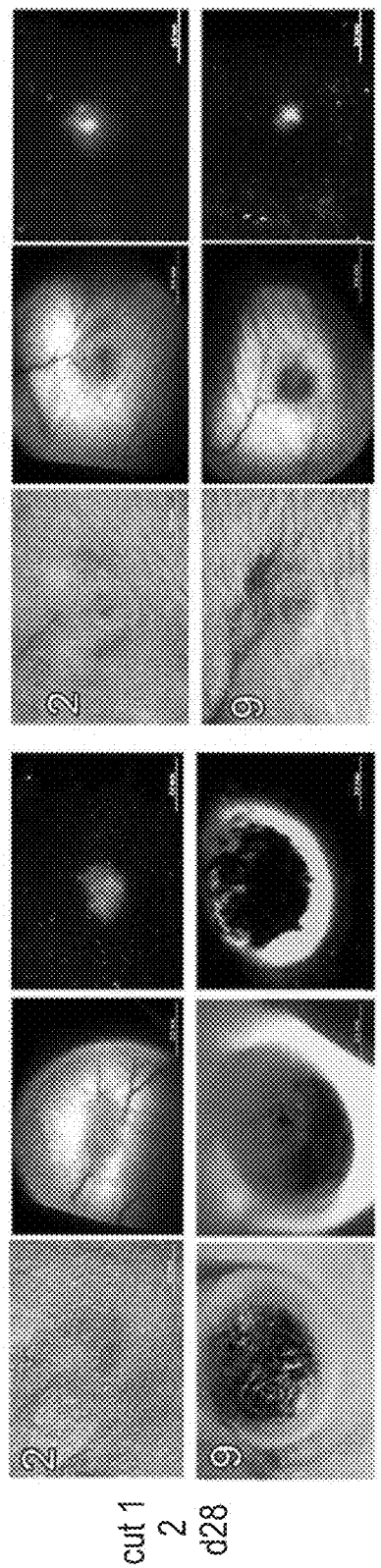
FIG. 11 includes pictures of a second tumor growing from cells injected 28 days after the first tumor was removed by surgical excision of the prior art.

FIG. 11 includes pictures of a second tumor growing from cells injected 28 days after the first tumor was removed by surgical excision of the prior art. The arrangement of pictures is the same of that as in FIG. 9.

The photographs show normal (control) growth of second tumors. One can see that the tumors grow essentially the same as the first tumors.

Figure 12:
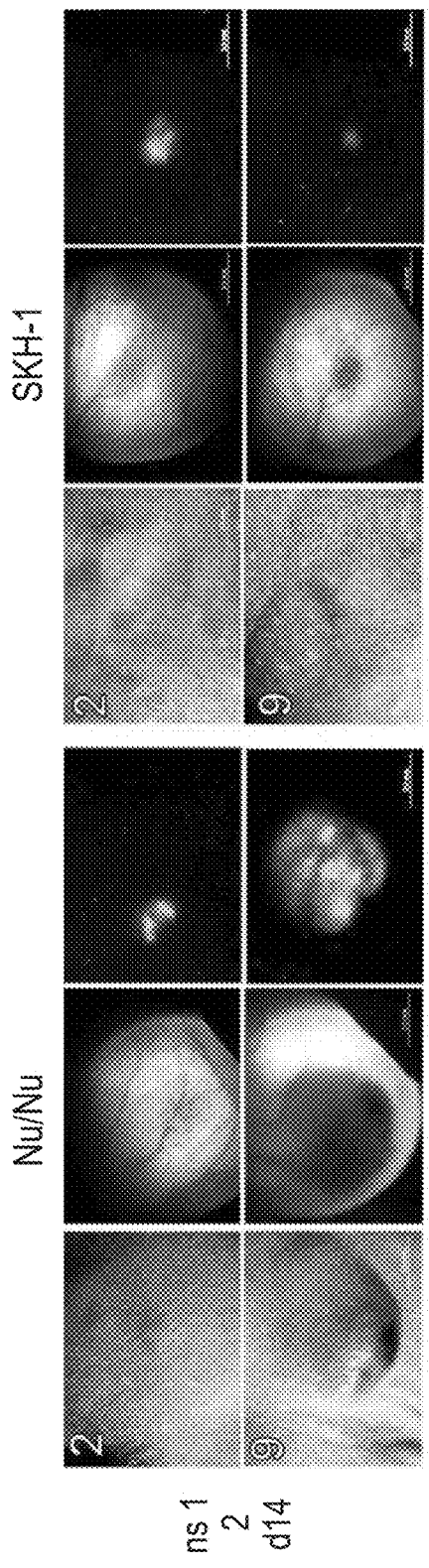
FIG. 12 includes pictures of a second tumor growing from cells injected 14 days after the first tumor was treated with nsPEF nanoelectroablation in accordance with an embodiment.

FIG. 12 includes pictures of a second tumor growing from cells injected 14 days after the first tumor was treated with nanoelectroablation in accordance with an embodiment. The arrangement of pictures is the same of that as in FIG. 9.

The photographs show a difference in secondary tumor growths between immunodeficient mice (Nu/Nu) and normal mice (SKH-1). One can see that the secondary tumor in the normal mice hardly grew, while the secondary tumor in the immunodeficient mice grew unabated. This demonstrates that the difference is caused by sufficient stimulation of the immune system by nsPEF.

Figure 13:
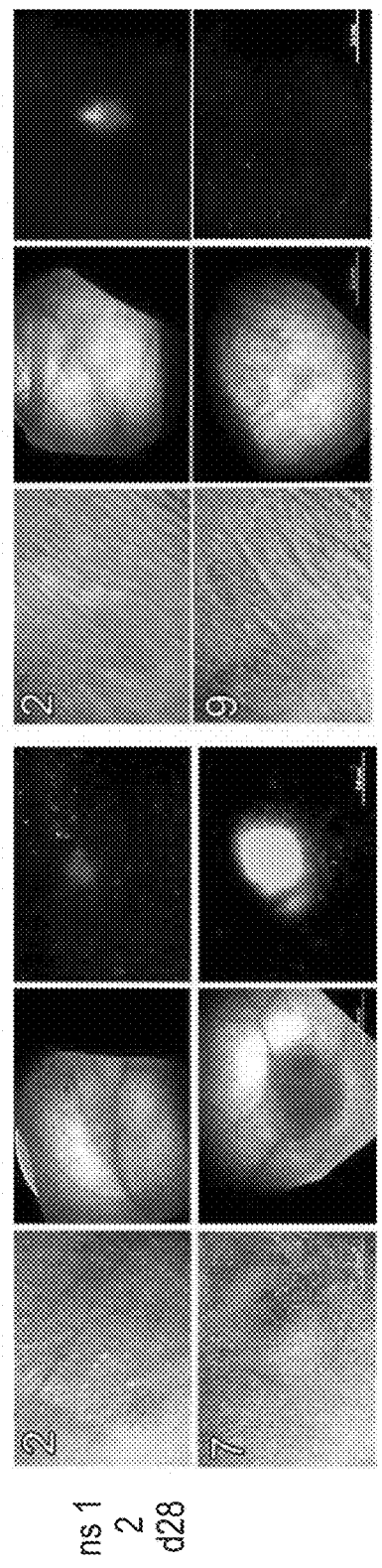
FIG. 13 includes pictures of a second tumor growing from cells injected 28 days after the first tumor was treated with nsPEF nanoelectroablation in accordance with an embodiment.

FIG. 13 includes pictures of a second tumor growing from cells injected 28 days after the first tumor was treated with nanoelectroablation in accordance with an embodiment. The arrangement of pictures is the same of that as in FIG. 9.

The photographs show a difference in secondary tumor growths between immunodeficient mice (Nu/Nu) and normal mice (SKH-1). One can see that the secondary tumor in the normal mice hardly grew, while the secondary tumor in the immunodeficient mice grew unabated. This demonstrates that the nsPEF-inspired stimulation of the immune system against secondary tumors is sufficient for tumors that are injected even after 28 days. That is, nsPEF treatment of a primary tumor stimulates the immune system for weeks or months on end, if not longer or permanently.

Figure 14:
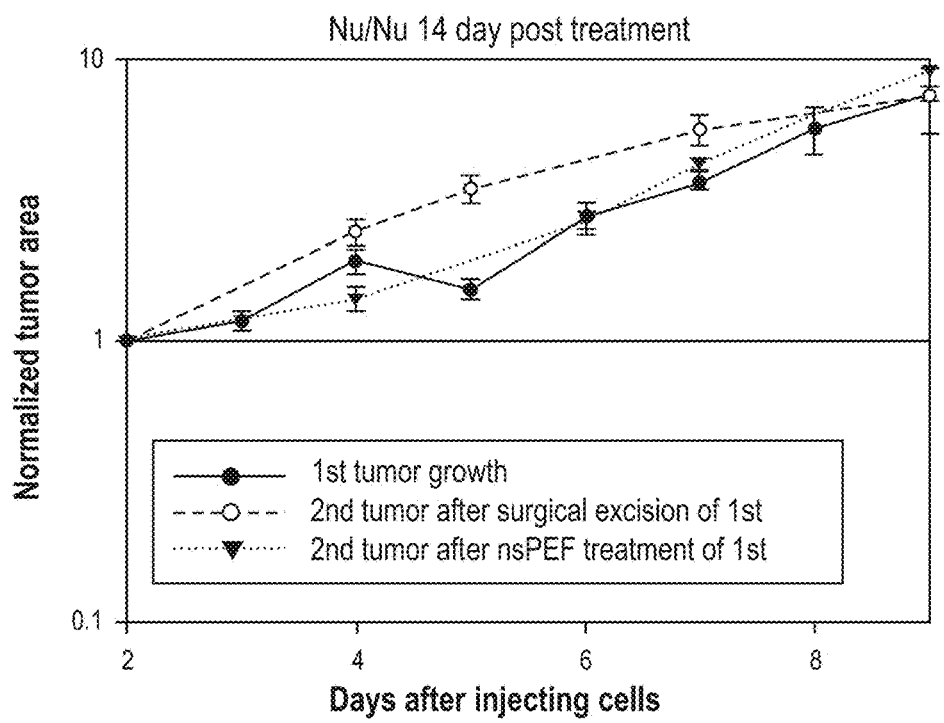
FIG. 14 is a line graph of tumor size versus time for immunosuppressed (Nu/Nu) mice in which the second tumor was injected 14 days after surgical removal or nano-electroablation in accordance with an embodiment.

FIG. 14 is a line graph of tumor size versus time for immunosuppressed (Nu/Nu) mice in which the second tumor was injected 14 days after surgical removal or nanoelectroablation in accordance with an embodiment. Each mean is an average of three separate experiments, and the bars represent SEM (standard error of mean).

Surgical removal and nsPEF does not appear to have any effect on secondary tumors in immunosuppressed mice.

Figure 15:
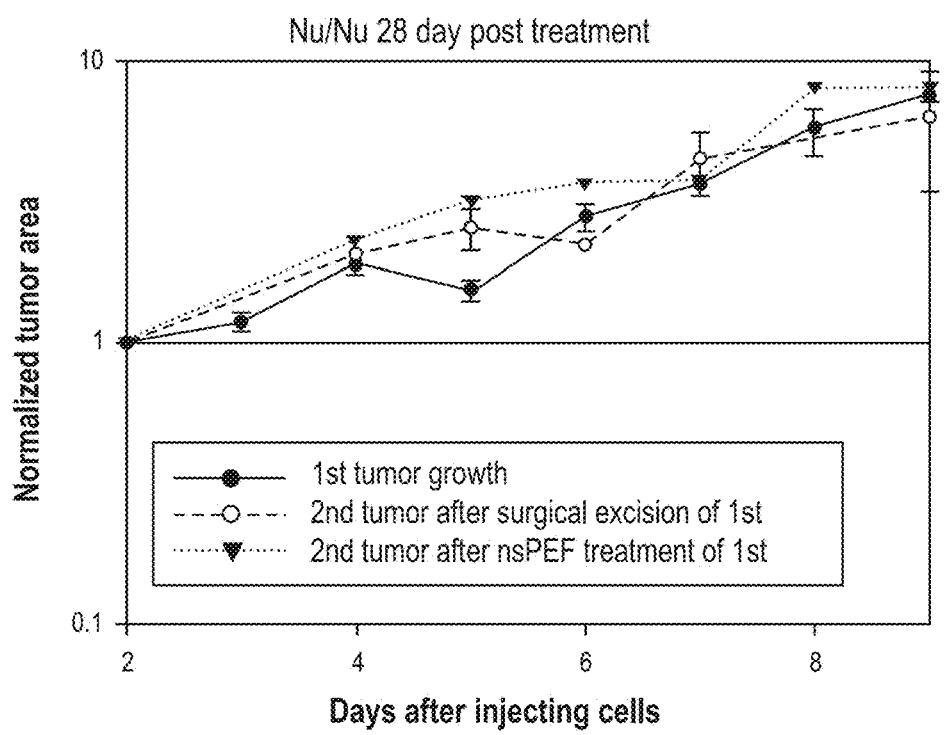
FIG. 15 is a line graph of tumor size versus time for immunosuppressed (Nu/Nu) mice in which the second tumor was injected 28 days after surgical removal or nano-electroablation in accordance with an embodiment.

FIG. 15 is a line graph of tumor size versus time for immunosuppressed (Nu/Nu) mice in which the second tumor was injected 28 days after surgical removal or nanoelectroablation in accordance with an embodiment. Each mean is an average of three separate experiments, and the bars represent SEM (standard error of mean).

Again, surgical removal and nsPEF does not appear to have any effect on secondary tumors in immunosuppressed mice.

Figure 16:
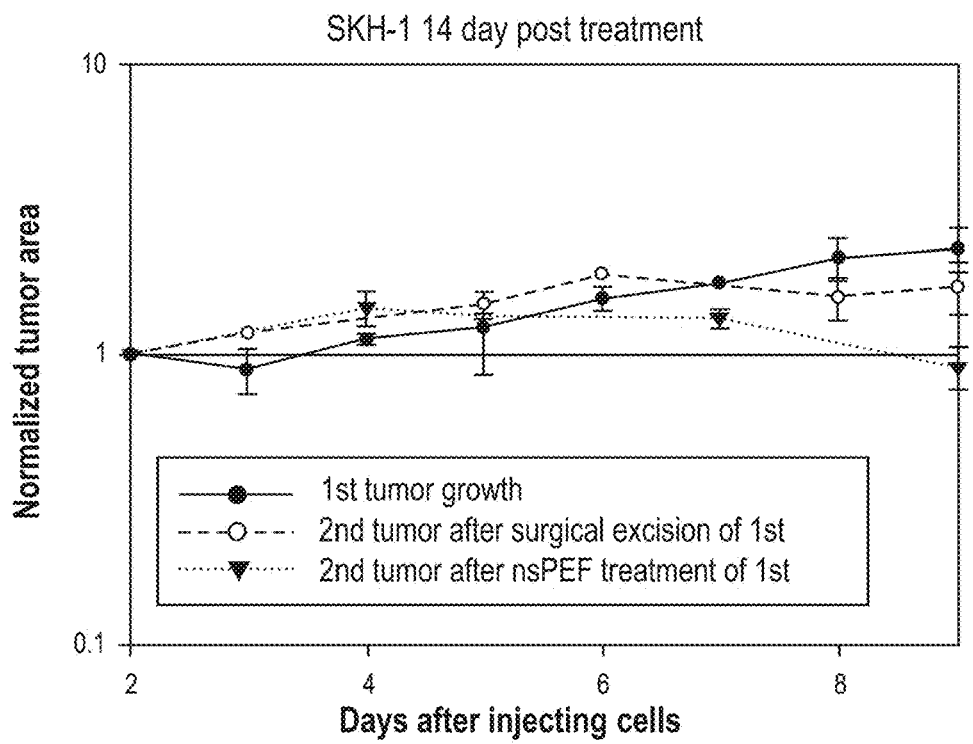
FIG. 16 is a line graph of tumor size versus time for immunocompetent (SKH-1) mice in which the second tumor was injected 14 days after surgical removal or nanoelectroablation in accordance with an embodiment.

FIG. 16 is a line graph of tumor size versus time for immunocompetent (SKH-1) mice in which the second tumor was injected 14 days after surgical removal or nanoelectroablation in accordance with an embodiment.

There is a striking difference between the growth of secondary tumors in which their primary tumors are subject to surgical removal or nsPEF. NsPEF of a primary tumor results in a secondary tumor shrinking in these immunocompetent mice.

Figure 17:
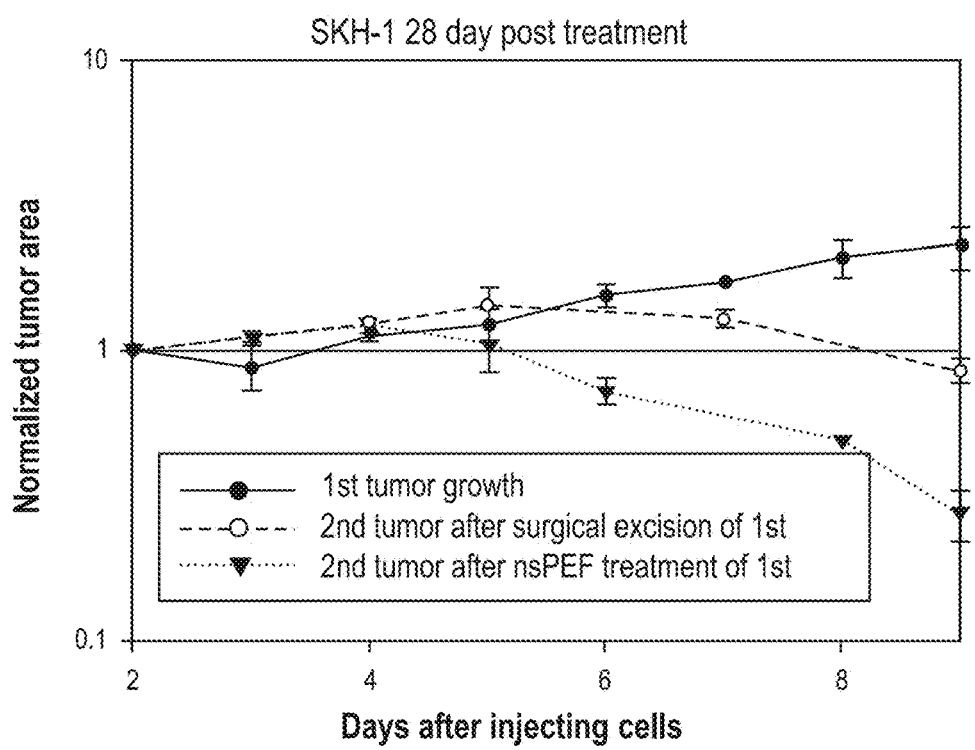
FIG. 17 is a line graph of tumor size versus time for immunocompetent (SKH-1) mice in which the second tumor was injected 28 days after surgical removal or nanoelectroablation in accordance with an embodiment.

FIG. 17 is a line graph of tumor size versus time for immunocompetent (SKH-1) mice in which the second tumor was injected 28 days after surgical removal or nanoelectroablation in accordance with an embodiment.

Again, there is a striking difference between secondary tumor growth rates. One secondary tumor decreased in size so substantially that it is evident on the logarithmic scale.

Immunodeficient mice showed no difference between the tumor growth rates of the initial and secondary tumors. However, in immunocompetent mice, most tumors injected 28 days after the first tumor was treated with nsPEF actually shrank. Immunohistochemical analysis of these tumors identified CD4+ cells within both the treated tumor as well as in untreated tumors in animals in which another tumor had been nanoelectroablated.

However, one drawback of this experiment was that the B16 melanoma cells were originally derived from C57BL/6 mice so that the SKH-1 strain recognized these B16 cells as foreign. Consequently, the controls in which the tumor was surgically removed rather than treated with nsPEF also exhibited some inhibition of secondary tumor growth, although to a lesser degree than that observed in mice with nsPEF-treated tumors.

In order to eliminate this complication, B6 albino mice derived from the C57BL/6 line were used for subsequent experiments. These B6 mice do not mount a measurable immune response against B16 melanoma cells; therefore, the secondary tumor grows just as fast as the primary tumor.

The inventors conducted two types of experiments with B6 albino mice. In the first, a single tumor was injected into several mice and either surgically removed or treated with nsPEF seven days post-injection when the tumors were 4 mm in diameter. In the second experiment, three primary tumors were injected and either surgically removed or treated with nsPEF seven days post injection. Twenty-eight days later, a secondary tumor was injected and its growth rate measured for 10-13 days. No inhibition of secondary tumor growth of the tumors in mice was observed in which the primary tumors were surgically removed. However, in experiments in which the primary tumors were treated with nsPEF, the secondary tumor injected 28 days later exhibited inhibited growth compared to the controls without a second nsPEF treatment. In two of the three treated mice, the secondary tumor actually shrank to about half of its original size by day ten (see FIG. 19).

Figure 18:
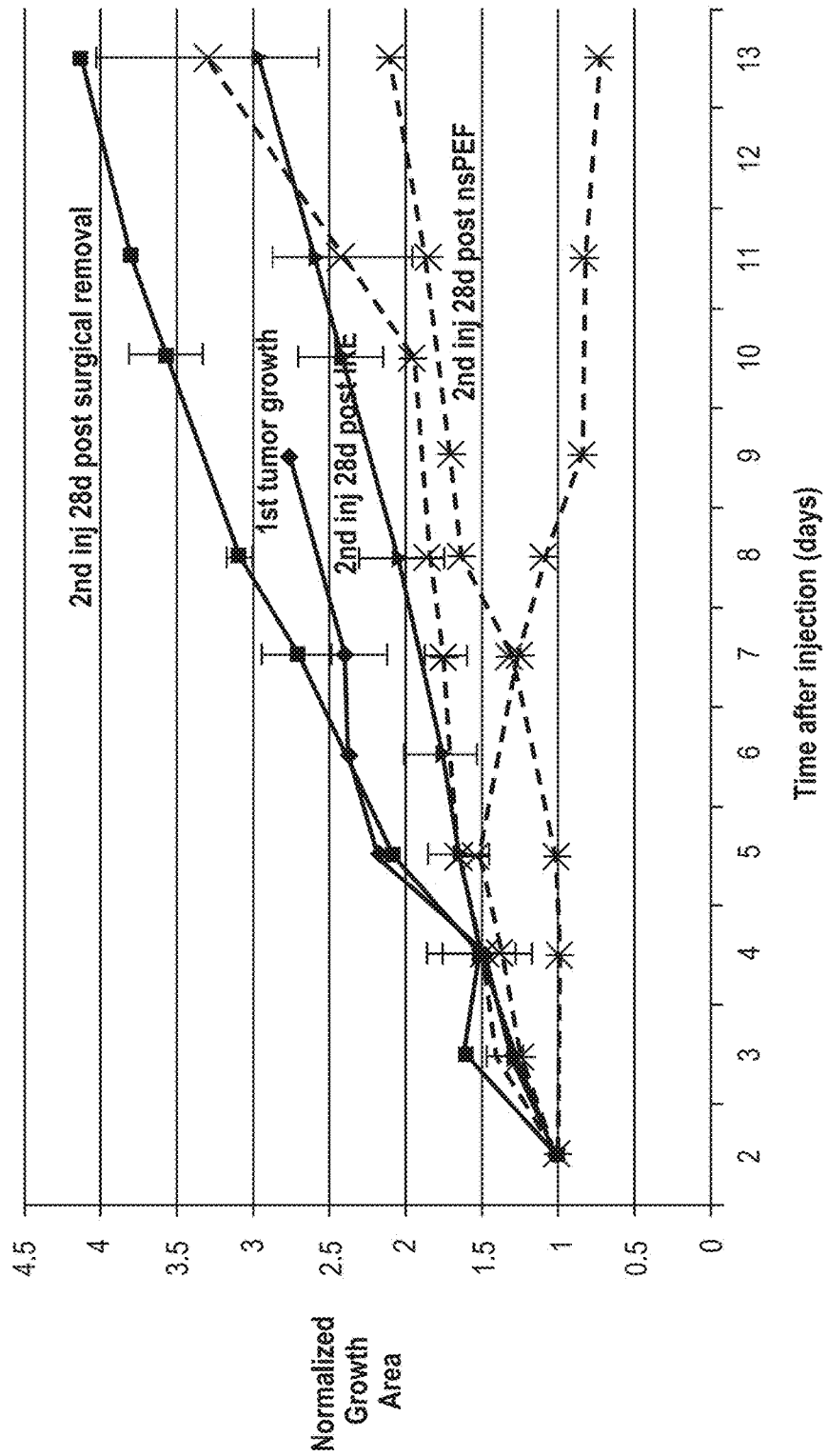
FIG. 18 is a graph comparing empirical results of secondary tumor growth between mice having surgically removed primary tumors (solid lines) and one nsPEF-treated primary tumor (dashed lines) in accordance with an embodiment.

FIG. 18 is a graph comparing empirical results of secondary tumor growth between mice having surgically removed primary tumors (solid lines) and one nsPEF-treated primary tumor (dashed lines) in accordance with an embodiment. One 4 mm-wide primary tumor was either treated with nsPEF or removed surgically followed by the injection of a second tumor 28 days later. Note that the dashed lines mostly fall below the solid lines, indicating that nsPEF treatments of primary tumors helps in halting growth (or shrinking) secondary tumors.

Figure 19:
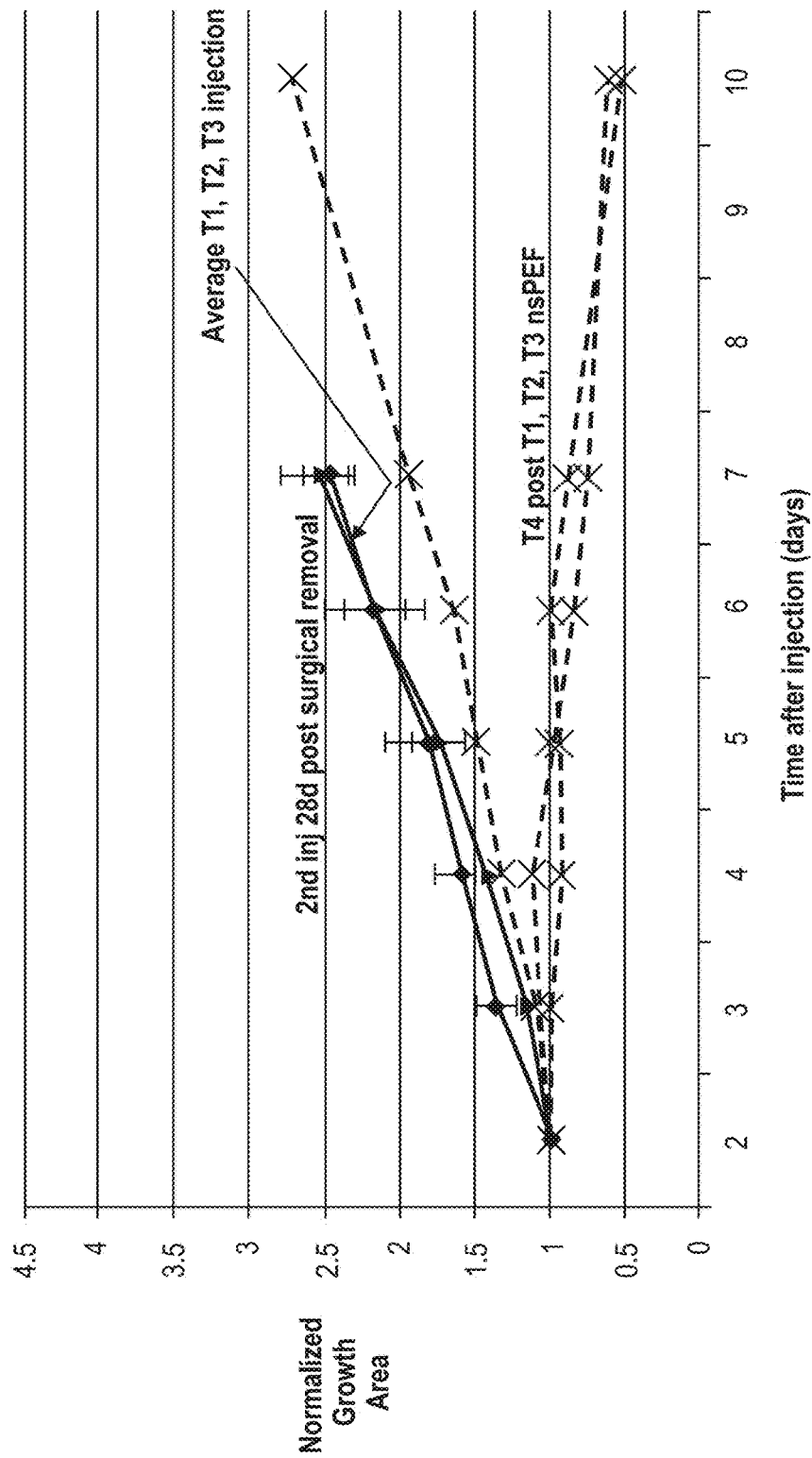
FIG. 19 is a graph comparing empirical results of secondary tumor growth between mice having surgically removed primary tumors (solid lines) and three nsPEF-treated primary tumors (dashed lines) in accordance with an embodiment.

FIG. 19 is a graph comparing empirical results of secondary tumor growth between mice having surgically removed primary tumors (solid lines) and three nsPEF-treated primary tumors (dashed lines) in accordance with an embodiment. Three 4 mm-wide tumors were treated with nsPEF or surgically removed followed by the injection of a second tumor 28 days later. Among a three-tumor data set, a clearer trend of dashed lines below solid lines is visible. A few of the nsPEF treatments resulted in secondary tumors shrinking to half (0.5) their size.

Secondary tumor growth is inhibited in B6 albino immunocompetent mice in which the first tree tumors were nanoelectroblated (three dashed line data sets marked with Xs) but not in mice in which the first three tumors are surgically removed (solid line data set marked with solid Os). The black line data set marked with diamonds represents the average growth of the primary tumors prior to removal or nanoelectroablation.

Figure 20:
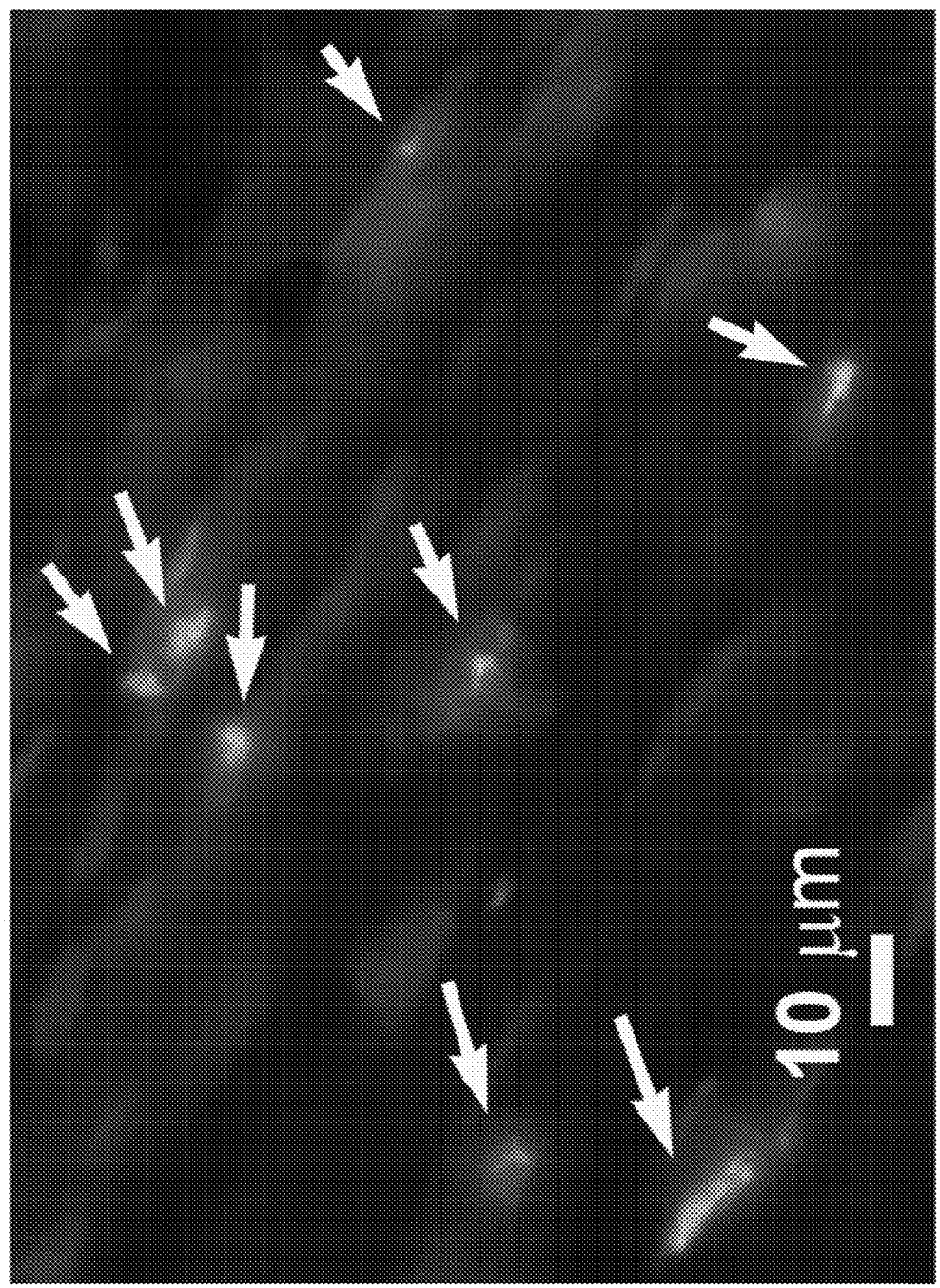
FIG. 20 is a histological section within a secondary tumor stained to show CD8+ cytotoxic T cells.

FIG. 20 is a histological section of a region within a secondary tumor stained with a fluorescent antibody to label CD8+ cytotoxic T cells, a result of nsPEF stimulation of primary tumors in accordance with an embodiment. This shows that the subject's immune system was sufficiently stimulated with nsPEF.

Figure 21B:
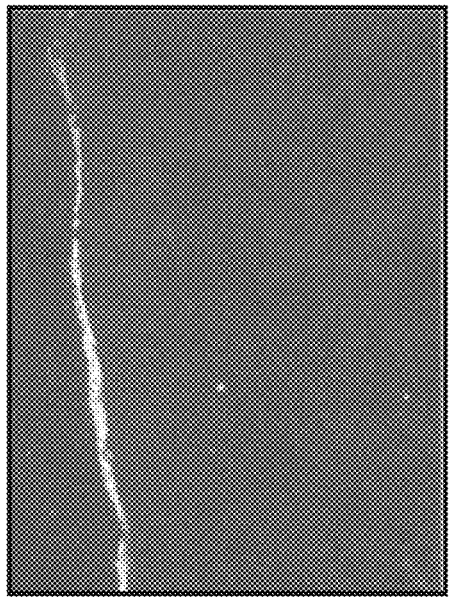
FIG. 21B is an image of the same region as in FIG. 21A but with fluorescent labeling.
Figure 21A:
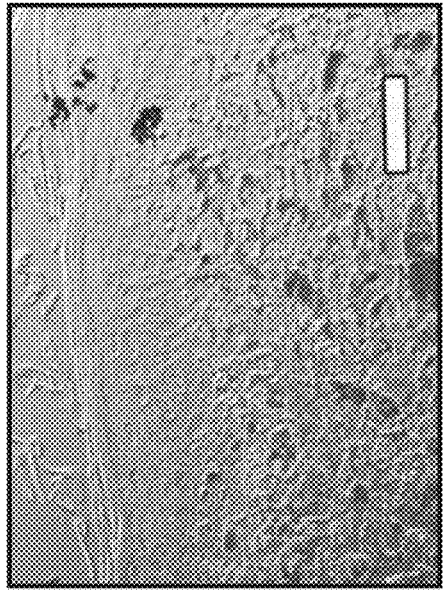
FIG. 21A is an image of an unstained, unbleached tumor section fixed 12 days after nsPEF treatment in accordance with an embodiment.

FIGS. 21A-21B are images of an unstained and fluorescently labeled tumor section, respectively, fixed 12 days after nsPEF treatment. The white scale bar represents 200 μm.

The fluorescent label from a CD4 antibody indicates surface labeling, but no T cells could be found within the tumor at this early time point.

Figure 22B:
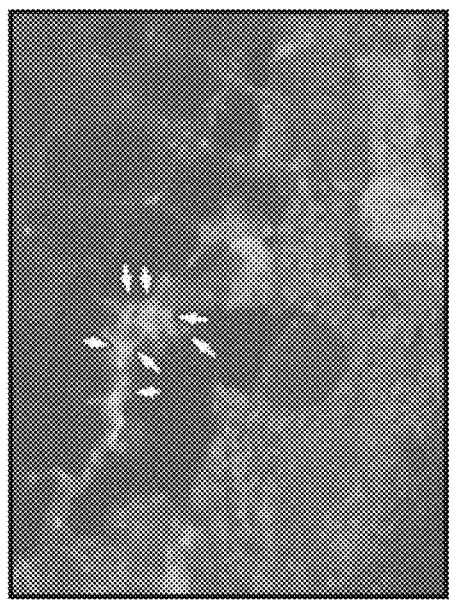
FIG. 22B is an image of the same region as in FIG. 22A but with fluorescent labeling.
Figure 22A:
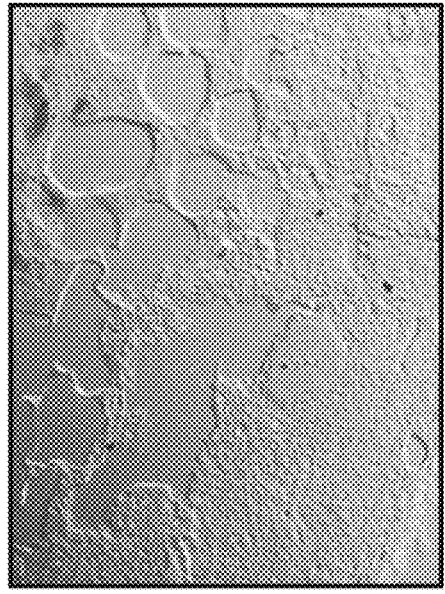
FIG. 22A is an image of an unstained, unbleached tumor section fixed 19 days after nsPEF treatment in accordance with an embodiment.

FIGS. 22A-22B are images of an unstained and fluorescently labeled tumor section, respectively, fixed 19 days after nsPEF treatment.

Superposition of both Hoechst and anti-CD4 fluorescence from the section shown indicates the presence of CD4+ T cells (arrows) within the tumor in FIG. 22B. That is, after 19 days of this primary tumor, CD4+ T cells were activated against the tumor.

Figure 23A:
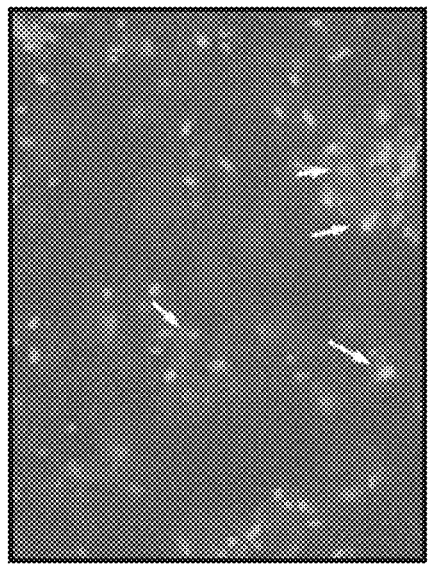
FIG. 23A is an image of an unstained, unbleached second tumor section fixed 19 days after nsPEF treatment of a first tumor in accordance with an embodiment.
Figure 23B:
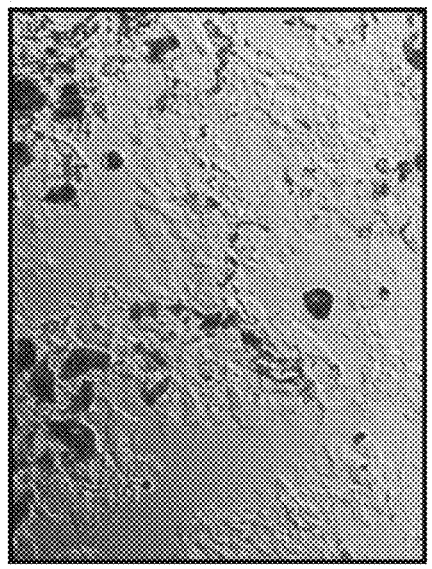
FIG. 23B is an image of the same region as in FIG. 23A but with fluorescent labeling.

FIGS. 23A-23B are images of an unstained and fluorescently labeled secondary tumor section, respectively, fixed 19 days after nsPEF treatment of a primary tumor.

Superposition of Hoechst and anti-CD4 fluorescent labels from the section shown indicates the presence of CD4+ T cells (arrows) within the (untreated) secondary tumor in FIG. 23B.

Figure 24A:
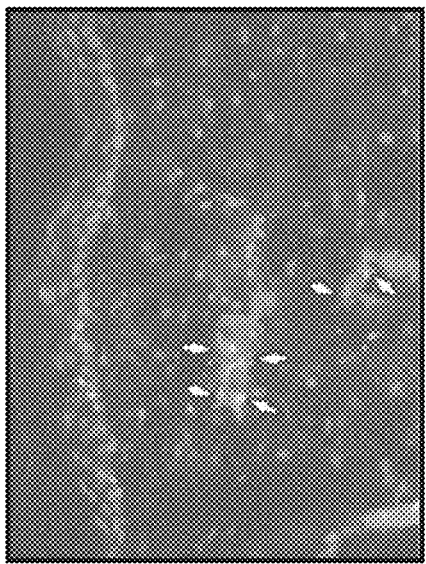
FIG. 24A is an image of an unstained, unbleached second tumor section fixed 32 days after nsPEF treatment of a first tumor in accordance with an embodiment.
Figure 24B:
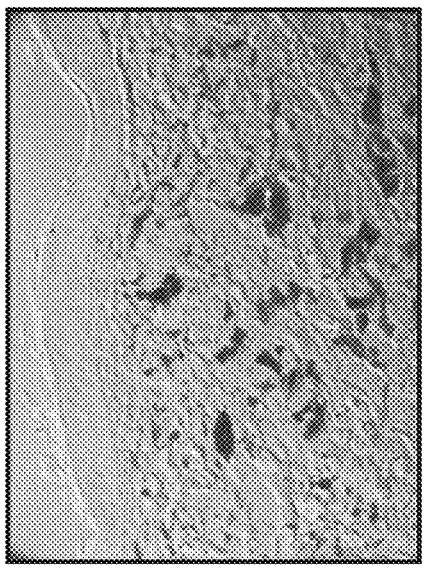
FIG. 24B is an image of the same region as in FIG. 24A but with fluorescent labeling.
Figure 25A:
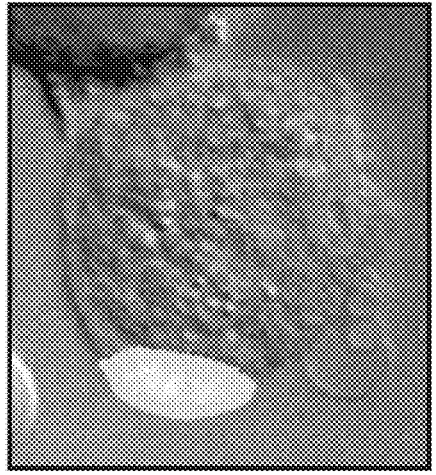
FIGS. 25A-25F are images of six different human pancreatic carcinoma cells with calreticulin labeling after nsPEF treatment in accordance with an embodiment.
Figure 25B:
Figure 25C:
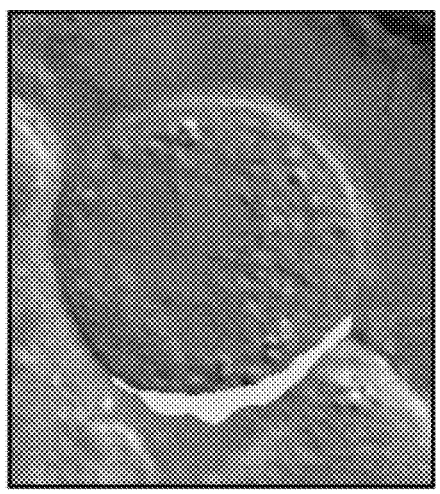
Figure 25D:
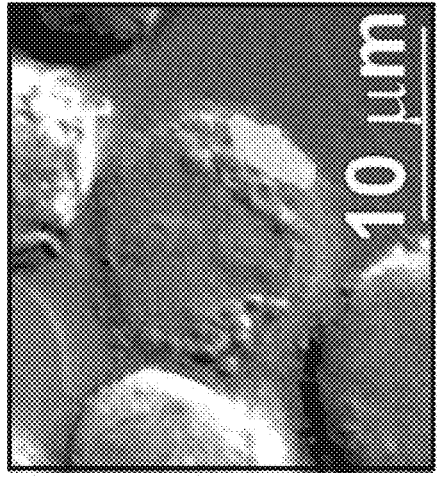
Figure 25E:
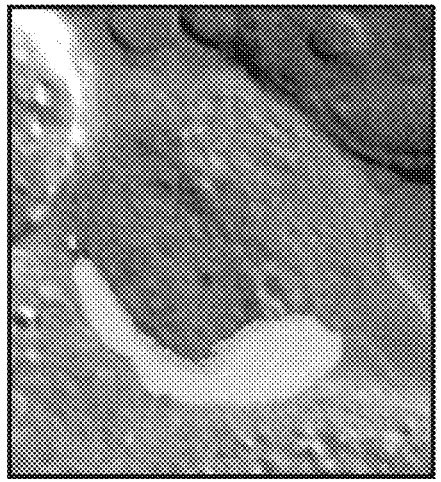
Figure 25F:
Figure 26A:
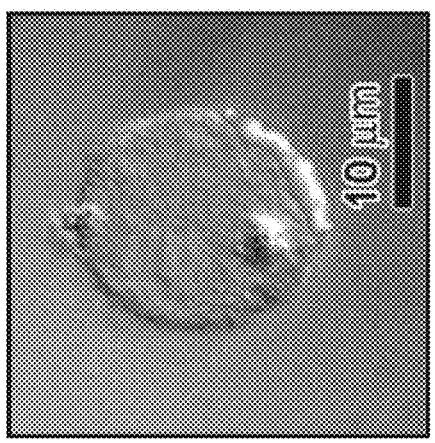
FIGS. 26A-26F are images of six different murine (mouse) squamous cell carcinoma cells with calreticulin labeling after nsPEF treatment in accordance with an embodiment.
Figure 26B:
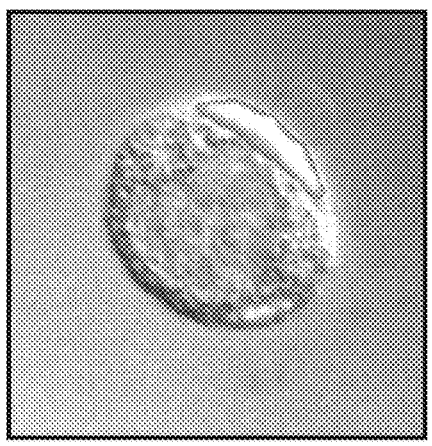
Figure 26C:
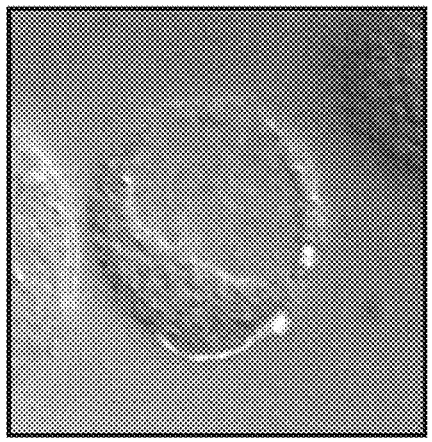
Figure 26D:
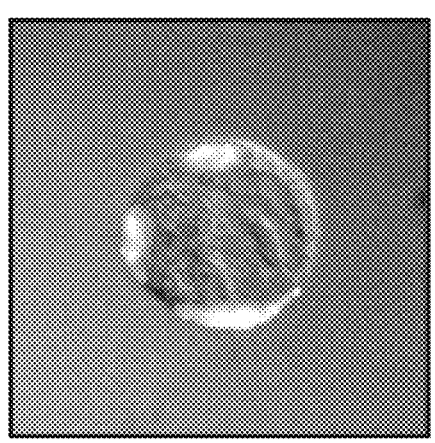
Figure 26E:
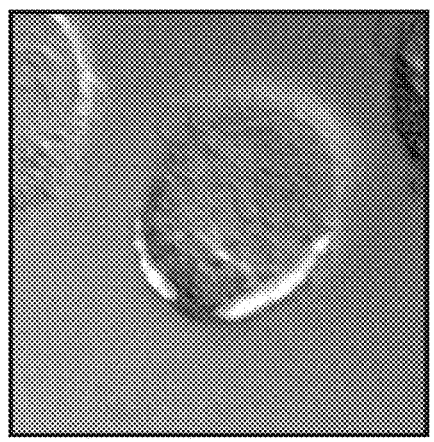
Figure 26F:
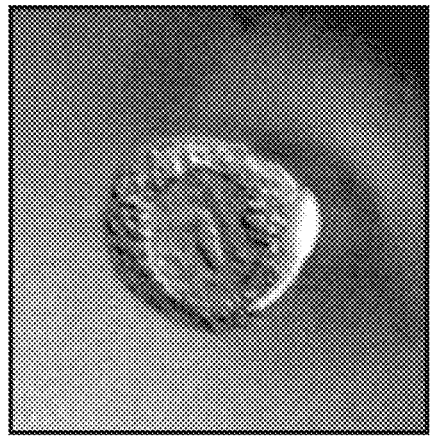

FIGS. 24A-24B are images of an unstained and fluorescently labeled second tumor section fixed 32 days after nsPEF treatment of a first tumor.

Superposition of Hoechst and anti-CD4 fluorescent labels from the section indicates the presence of CD4+ T cells (arrows) are found within this untreated (i.e., not directly treated by nanoelectroablation) tumor.

Each of FIGS. 21-24 illustrate the arrival of CD4+ T cells against the primary (directly treated) and secondary (untreated) tumors, a result of proper nsPEF stimulation.

FIGS. 25A-25F are images of six different human pancreatic carcinoma cells with calreticulin labeling after nsPEF treatment in accordance with an embodiment. Labeled with fluorescent anti-calreticulin antibody, the figures indicate the translocation of calreticulin to the respective human pancreatic carcinoma cell surfaces following nsPEF stimulation.

The figures shows human pancreatic carcinoma cells that were fixed and labeled two hours after being treated with 15 pulses of 25 kV/cm and 100 ns. It does not take long for calreticulin to be detectable on the surface membranes of the tumor cells after nsPEF treatment.

FIGS. 26A-26F are images of six different murine (mouse) squamous cell carcinoma cells with calreticulin labeling after nsPEF treatment in accordance with an embodiment. Labeled with fluorescent anti-calreticulin antibody, the figures indicate the translocation of calreticulin to the respective murine squamous cell carcinoma cell surfaces following nsPEF stimulation.

The figures shows murine squamous cell carcinoma cells that were fixed and labeled two hours after being treated with 25 pulses of 25 kV/cm and 100 ns.

Calreticulin is a protein normally found in the endoplasmic reticulum in the cell interior. Some treatments that trigger apoptosis have been found to stimulate the translocation of this protein to the plasma membrane where it serves as an additional "eat me" signal for white blood cells. It is a member of the Damage-Associated Molecular Pattern (DAMPs) family that has been shown to stimulate an immune response against the cells exhibiting those proteins on their surface.

Such sampling of tumor cells for calreticulin can be used to ensure proper, sufficient, and optimized stimulation of the immune system. For example, calreticulin can be detected on 0.5%, 1%, 2%, 3%, 4%, 5%, 7%, 10%, 12%, 15%, 20%, 25%, 30%, 33%, or more of the surface of a cell can indicate that it is sufficiently expressed for purposes of stimulating an immune response. The amount of calreticulin may be chosen in order to optimize immune response. The amount of calreticulin expression in a series of tumor cells can be controlled by the electric field intensity (e.g., voltage per centimeter), pulse width, number of pulses, and duty cycle of the pulses of the nsPEF treatment. The electrical current flowing through the cells may be indirectly controlled by the electric field intensity, a current limiter, or as otherwise known in the art.

Figure 27:
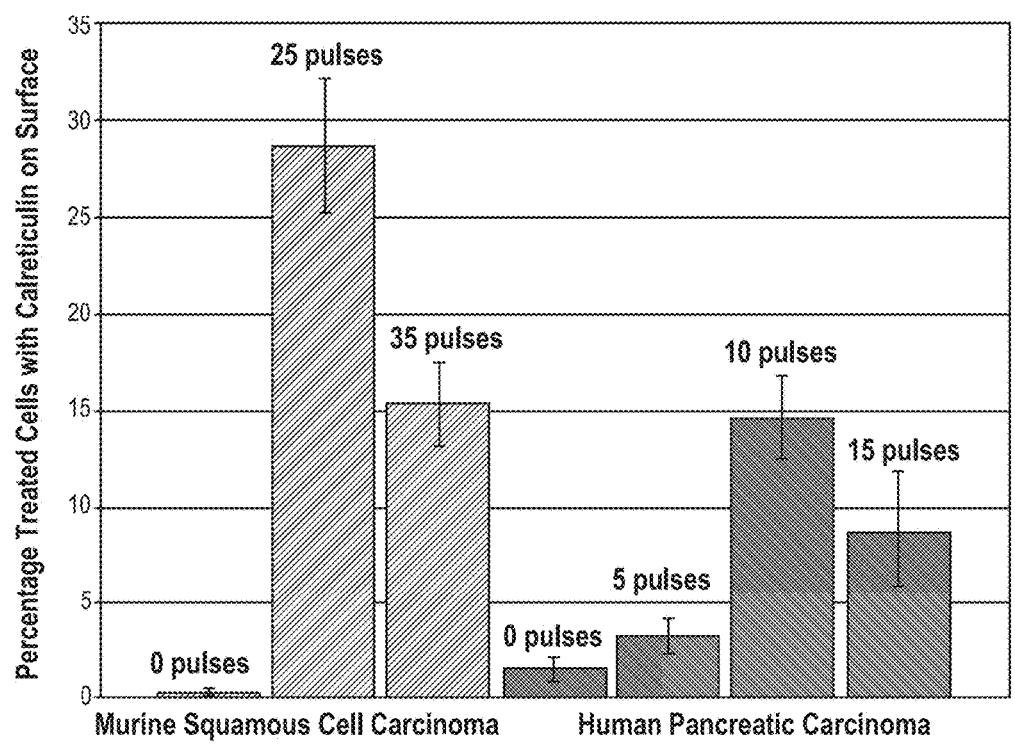
FIG. 27 is a graph showing percentages of cells that express calreticulin on their surface membranes after nsPEF treatment in accordance with an embodiment.

FIG. 27 is a graph showing percentages of cells that express calreticulin on their surface membranes after nsPEF treatment in accordance with an embodiment. Relative percentages are shown of both murine squamous cell carcinoma cells and human pancreatic carcinoma cells exhibiting calreticulin on their surface in response to nsPEF treatment at various pulse numbers (i.e., 25 kV/cm, 100 ns for the exemplary embodiment). As shown for isolated human pancreatic carcinoma tumors, 10 pulses maximized calreticulin expression. A maximum calreticulin expression peak may be optimized by the number of pulses.

For murine squamous cell carcinoma cells, 25 pulses triggers CRT translocation in nearly 30% of the treated cells. This treatment was done in a cuvette with parallel plates 2 mm to 4 mm apart. The cells were floating free in the medium rather than packed densely in a tumor. Under these conditions, the cells are more sensitive to the imposed field and respond to much lower pulse numbers than when they are in a tumor in vivo.

FIG. 28A is an image of a primary liver tumor 1 week after the injection of tumor cells into the liver and just before it was nsPEF treated. After the FIG. 28A photograph was taken, the tumor was subject to nsPEF treatment. After three weeks, the first tumor was completely ablated and a second injection of tumor cells was made into the same liver. One week later, the FIG. 28B photograph was taken of the secondary tumor. The much smaller size of this second tumor after the same growth period of 1 week suggests that the immune system was inhibiting the growth of the second tumor.

To rule out that the immune system was being stimulated by the tumor cells themselves (as foreign objects to the body), syngeneic (i.e., genetically identical) tumor cells were used. These tumors were generated by injecting $10^6$ McA-RH7777 rat liver tumor cells into the liver of a Buffalo rat.

Figure 29A:
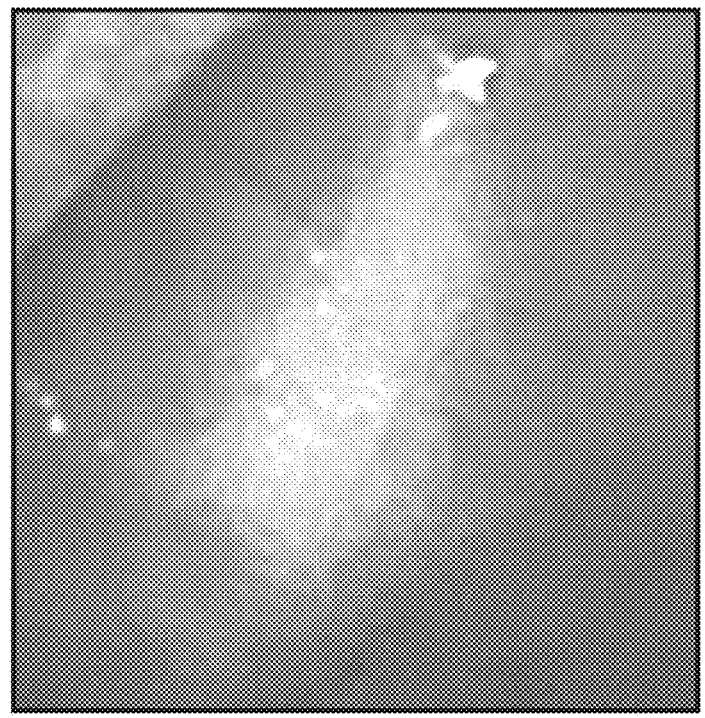
FIG. 29A is an image of a primary liver tumor one week after injection.
Figure 29B:
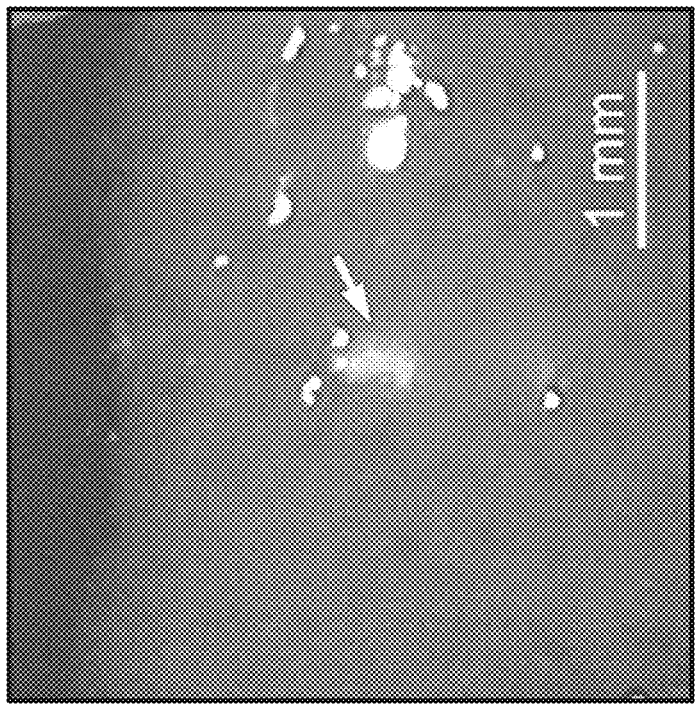
FIG. 29B is an image of a secondary liver tumor one week after injection of tumor cells that took place three weeks after nsPEF treatment of the first tumor (in FIG. 29A) in accordance with an embodiment.

FIG. 29A is an image of a primary liver tumor after one week of growth, just before it is nsPEF treated. After the FIG. 29A photograph was taken, the tumor was subjected to nsPEF treatment. After three weeks, a second injection of tumor cells was made in the liver. After one week of growth, the FIG. 29B photograph was taken of the secondary tumor. The growth of the secondary tumor was strongly inhibited, and the tumor size after 1 week of growth was 95% smaller on average than the size of the first tumor after 1 week of growth.

The figure provides evidence that nanoelectroablation of a liver tumor triggers an immune response against the treated tumor. The second injection of the same number of tumor cells into a different liver lobe results in a strong inhibition of tumor growth that is probably due to an immune response as found with the second melanoma tumor injection described above.

Applying nsPEF to a tumor sufficient to stimulate apoptosis includes at least the electrical characteristics found experimentally. For example, a 100 ns long pulse with a 20 ns rise time to 30 kV/cm (kilovolts per centimeter) at 1 to 7 pulses per second (pps) for 500 to 2000 pulses has been found to be sufficient to stimulate apoptosis, depending on the tumor type. Pulsed electric fields of at least 20 kV/cm have been shown to be effective. A number of pulses greater than 50 pulses has also been shown to be effective. Current values between 12 A and 60 A resulted, depending on the electrode type and skin resistance.

For a 2-pole parallel plate, the frequency was 7 pps, and for needle electrodes, the frequency was lowered to 5 pps. If tumor regrowth occurred, one or more other treatments were applied until there was no sign of recurrence.

Measuring an immune response biomarker between 14 and 28 days has been shown to be an effective time period for determining whether the nanoelectroablation treatment successfully stimulated an immune response. Gauging an immune response biomarker before treatment and then comparing the immune response biomarker after treatment to the pre-treatment biomarker can result in a better measure of immune response in some situations.

Subsequent nanoelectroablation treatment of the same or a different tumor can re-stimulate an immune response or begin stimulating an immune response if the first treatment was unsuccessful. A quantified sensitivity of the tumor cells to nsPEF can include a measured growth or reduction in size in a tumor at a specified time after nsPEF therapy.

Stimulation of Immune Response

It has been surprisingly found that an nsPEF that is applied to a tumor in a subject can stimulate the production of an immune response to the tumor in the subject. Without being bound to a particular theory, it is believed that application of the nsPEF to the tumor stimulates, promotes, or potentiates immunogenic apoptosis in the tumor cell and that subsequently, an immune response to the tumor cells or cell fragments is stimulated. The immune response to the tumor cells inhibits subsequent tumor growth (e.g., metastatic tumor growth). Thus, stimulating immunogenic apoptosis of tumor cells results in the stimulation of an immune response to the tumor cells that can delay and/or inhibit the growth of subsequent tumors in the subject, reduce the size of subsequent tumors in the subject, delay and/or inhibit tumor metastasis in the subject, and/or reduce the size or spread of metastatic tumors in the subject.

Thus, in one aspect the present invention relates to methods of stimulating an immune response to a tumor in a subject by applying a nsPEF to the tumor to stimulate apoptosis of the tumor cells and stimulating the production of an immune response to the tumor cells. In another aspect, the present invention relates to methods of preventing subsequent tumor growth (e.g., metastatic tumor growth) in a subject by applying a nsPEF to the tumor to stimulate apoptosis of the tumor and stimulating the production of an immune response to the tumor cells.

A nsPEF treatment that is sufficient to stimulate an immune response may do so by causing the tumor to express calreticulin (CRT) on surface membranes of its tumor cells. CRT is a well-documented DAMP that can function as either adjuvant or danger signals for the innate immune system of a subject. Some DAMPs become enriched on the outer leaflet of plasma membranes, such as calreticulin and HSP90. These DAMPs can have a beneficial role in cancer therapy by stimulating an immune system. It has been demonstrated that blockade or knockdown of calreticulin suppresses the phagocytosis of anthracyclin-treated tumor cells by dendritic cells and abolishes their immunogenicity in mice (Obeid et al., "Calreticulin exposure dictates the immunogenicity of cancer death cells," *Nature Medicine*, January 2007, volume 13(1), pages 54-61). It has also been shown that the amount of phagocytosis by dendritic cells is directly proportional to the amount of calreticulin expression on cell surfaces of a target cell. The inventors have demonstrated with their nsPEF equipment that it can trigger calreticulin on the cell surface of treated cells. This expression of calreticulin on surface membranes of tumor cells then stimulates the subject's immune response.

Cancer that has metastasized through a subject's bloodstream may be treated using nsPEF's immune stimulation properties. For treatment, circulating tumor cells (CTCs) are isolated from the bloodstream and amassed in vial, test tube, or other suitable in vitro environment. In some cases, there may only be a few (e.g., 5, 10), tumor cells that are collected and amassed. Through this mass, an nsPEF electric field is applied in order to treat the cells. This may or may not cause calreticulin to be expressed on the surface membranes of the tumor cells. The tumor cells may then be introduced back into the subject's bloodstream by injection, infusion, or otherwise.

In an alternative embodiment, single CTCs may also be isolated from the bloodstream, and each tumor cell treated individually. An automated system that captures CTCs in whole blood using iron nanoparticles coated with a polymer layer carrying biotin analogues and conjugated with antibodies for capturing CTCs can automatically capture the tumor cells, and a magnet and or centrifuge can separate them. After separation from the antibodies, the CTCs may be treated with nsPEF through a small capillary and then reintroduced to the patient's bloodstream.

The treated CTCs, with calreticulin expressed, can trigger an immune response in the subject against the cancer. A technical advantage of this method is that invasive surgery to remove a tumor may be avoided by simply treating CTCs. Further, a large number of tumors may be addressed at one time simply by triggering the body's own immune response. In vivo electroshocks, and their associated side effects, are avoided.

In another embodiment, in vivo electroshocks and invasive surgery may wish to be avoided. A biopsy may be performed to remove a sample of tumor cells from one or a subset of multiple tumors within a patient. The sample may be cut, split from, peeled, or otherwise dissociated from the tumor. The sample is then subject to nsPEF treatment. After treatment, an assay confirms that treated samples have been effectively ablated, experience apoptosis so that they will no longer divide, and/or sufficiently express calreticulin on surface membranes of tumor cells of the sample. After confirmation, the biopsy samples are re-injected or otherwise reintroduced into the patient. A technical advantage of this over treating CTCs is that a much larger number of cells may be treated and reintroduced into the patient.

While examples in the application discuss human and murine subjects, the treatment of other animals is contemplated. Agricultural animals, such as horses and cows, or racing animals, such as horses, may be treated. Companion animals, such as cats and dogs, may find special use with the treatments described herein. It may be difficult for a veterinarian to remove many tumors from a small animal, and cancers may be caught relatively late because the animals cannot communicate their advancing pain. Further, the risk inherent in reinjecting tumor cells—albeit treated tumor cells—may be worth the potential benefits of potentially halting a metastasized cancer in a loved pet.

The methods of the present invention can be used for the treatment of any type of cancer, whether characterized as malignant, benign, soft tissue, or solid, and cancers of all stages and grades including pre- and post-metastatic cancers. Examples of different types of cancer include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer; ovarian cancer; renal cancer (e.g., renal cell carcinoma); cancer of the central nervous system; skin cancer (e.g., melanoma); lymphomas; gliomas; choriocarcinomas; head and neck cancers; osteogenic sarcomas; and blood cancers.

Electrical characteristics of nsPEF treatments can be adjusted based on a size and/or a type of a tumor. Types of tumors may include tumors of different regions of the body, such as the cancerous tumors described above.

Measuring a Stimulated Immune Response

In some embodiments, the methods of the present invention comprise applying a nanosecond pulsed electric field (nsPEF) to a tumor in a subject and measuring the stimulation of immune response to the tumor in the subject. As used herein, the term "measuring the stimulation of immune response" in a subject includes determining the presence or level of one of more biomarkers of immune response in one or more samples from the subject by using any quantitative or qualitative assay known to one of skill in the art. In some embodiments, an immune response is stimulated in a subject if the level of expression of one or more biomarkers of immune response (e.g., 1, 2, 3, 4, 5, 6, 7, 8, 9, 10 or more biomarkers) is above a threshold level (e.g., a threshold level determined based on an average or mean level of immune response in a subject or population of subjects having the same type of tumor). In some embodiments, an immune response is stimulated in a subject if the level of expression of one or more biomarkers of immune response (e.g., 1, 2, 3, 4, 5, 6, 7, 8, 9, 10 or more biomarkers) is increased by at least 5%, 10%, 15%, 20%, 25%, 30%, 35%, 40%, 45%, 50%, 60%, 70%, 80%, 90% or more relative to a control (e.g., a sample from the subject prior to the application of the nsPEF, or a sample from a control subject in which the nsPEF has not been applied).

For measuring one or more biomarkers of immune response, one or more biological samples from the subject can be used. In some embodiments, the sample is from whole blood, plasma, serum, saliva, urine, stool, tears, any other bodily fluid, tissue samples (e.g., biopsy), and cellular extracts thereof (e.g., red blood cellular extract). In one embodiment, the sample is a serum sample. The use of samples such as serum, saliva, and urine is well known in the art (see, e.g., Hashida et al., *J. Clin. Lab. Anal.*, 11:267-86 (1997)). One skilled in the art will appreciate that samples such as serum samples can be diluted prior to the analysis of biomarker levels. In some embodiments, the sample is a biopsy.

Biomarkers of Immune Response

In some embodiments, the biomarker of immune response is a white blood cell, for example, but not limited to a lymphocyte. In some embodiments, the biomarker of immune response is a T cell. Examples of T cells include, but are not limited to, CD4+ T cells and CD8+ T cells. In some embodiments, the biomarker of immune response is a cell that is positive for one or more of the CD markers CD3, CD4, CD8, CD16, or CD56.

In some embodiments, the biomarker of immune response is a cytokine. The term "cytokine" includes any of a variety of polypeptides or proteins secreted by immune cells that regulate a range of immune system functions and encompasses small cytokines such as chemokines. In some embodiments, the biomarker of immune response is an inflammatory cytokine. In some embodiments, the biomarker of immune response is a cytokine selected from GM-CSF, IL2, IL-4, IL-5, IL-6, IL-10, IL-12, IL-13, IL-15, interferon-γ, or TNF-α.

In some embodiments, the biomarker of immune response is a polypeptide or protein that is produced in an inflammatory or immune response. In some embodiments, the biomarker of immune response is acute phase protein, including but not limited to C-reactive protein (CRP) or serum amyloid A.

In some embodiments, the biomarker of immune response is an antibody to a tumor cell surface marker. As used herein, the term "antibody" includes a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab)$_2$ is included within the meaning of the term antibody. In some embodiments, the biomarker of immune response is an antibody to a cell surface tumor-associated antigen (TAA). In some embodiments, the biomarker of immune response is an antibody to a tumor cell surface marker selected from Human Epidermal Growth Factor Receptor 2 (HER2), Epidermal Growth Factor Receptor (EGFR), Carbonic Anhydrase IX (CAIX), Vascular Endothelial Growth Factor Receptor (VEGFR), VEGFR2, c-Met, prostate stem cell antigen (PSCA), Epithelial-Specific Cell Adhesion Activation Molecule (EpCAM), carcinoembryonic antigen (CEA), or CA-125.

In some embodiments, stimulation of an immune response is measured by determining the level or concentration of one or more biomarkers of immune response (e.g., 1, 2, 3, 4, 5, 6, 7, 8, 9, 10 or more biomarkers of immune response) selected from the group consisting of a white blood cell, a CD4$^+$ T cell, a CD8+ T cell, a natural killer T cell, GM-CSF, IL2, IL-4, IL-5, IL-6, IL-10, IL-12, IL-13, IL-15, interferon-γ, TNF-α, C-reactive protein, serum amyloid A, and an antibody to a tumor cell surface marker (e.g., a cell surface tumor-associated antigen (TAA), Human Epidermal Growth Factor Receptor 2 (HER2), Epidermal Growth Factor Receptor (EGFR), Carbonic Anhydrase IX (CAIX), Vascular Endothelial Growth Factor Receptor (VEGFR), VEGFR2, c-Met, prostate stem cell antigen (PSCA), Epithelial-Specific Cell Adhesion Activation Molecule (EpCAM), carcinoembryonic antigen (CEA), or CA-125). One skilled in the art will recognize that other tumor cell surface markers are suitable for use in the present invention.

Assays for Measuring Stimulation of Immune Response

Any of a variety of assays, techniques, and kits known in the art can be used to measure the stimulation of immune response in a sample. In some embodiments, a qualitative assay is used to determine whether the concentration or level of the one or more biomarkers of immune response is above a threshold level or is increased relative to a control. In some embodiments, a quantitative assay is used to determine the relative or absolute amount of the one or more biomarkers of immune response, e.g., for determining whether the concentration or level of the one or more biomarkers of immune response is above a threshold level or is increased relative to a control.

In some embodiments, the concentration or level of a biomarker of immune response (e.g., a white blood cell, a cytokine, a protein produced in an inflammatory or immune response, or an antibody to a tumor cell surface marker) is measured by flow cytometry. Flow cytometry methods and instrumentation are known in the art. Descriptions of instrumentation and methods can be found, e.g., in Introduction to Flow Cytometry: A Learning Guide (2000) Becton, Dickinson, and Company; McHugh, "Flow Microsphere Immunoassay for the Quantitative and Simultaneous Detection of Multiple Soluble Analytes," Methods in Cell Biology 42, Part B (Academic Press, 1994).

In some embodiments, the concentration or level of a biomarker of immune response (e.g., a white blood cell, a cytokine, a protein produced in an inflammatory or immune response, or an antibody to a tumor cell surface marker) is measured by phage display. For example, phage display technology for expressing a recombinant antigen specific for an antibody biomarker (e.g., an antibody to a tumor cell surface marker) can also be used to determine the presence or level of the antibody biomarker. Phage particles expressing an antigen specific for, e.g., an antibody marker, can be anchored, if desired, to a multi-well plate using an antibody such as an anti-phage monoclonal antibody (Felici et al., "Phage-Displayed Peptides as Tools for Characterization of Human Sera" in Abelson (Ed.), *Methods in Enzymol.*, 267, San Diego: Academic Press, Inc. (1996)).

In some embodiments, the concentration or level of a biomarker of immune response (e.g., a white blood cell, a cytokine, a protein produced in an inflammatory or immune response, or an antibody to a tumor cell surface marker) is measured by immunoassay. A variety of immunoassay techniques, including competitive and non-competitive immunoassays, can be used to determine the concentration or level of the one or more biomarkers of immune response. See, e.g., Self and Cook, *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (META); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser-induced fluorescence (see, e.g., Schmalzing and Nashabeh, *Electrophoresis*, 18:2184-2193 (1997); Bao, *J. Chromatogr. B. Biomed. Sci.*, 699:463-480 (1997)). Liposome immunoassays, such as flow-injection liposome immunoassays and liposome immunosensors, are also suitable for use in the present invention (see, e.g., Rongen et al., *J. Immunol. Methods*, 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., *J. Clin. Chem. Clin. Biol. Chem.*, 27:261-276 (1989)).

In some embodiments, antigen capture ELISA can be used to determine the presence or level of one or more biomarkers of immune response in a sample. For example, in an antigen capture ELISA, an antibody directed to a marker of interest is bound to a solid phase and sample is added such that the marker is bound by the antibody. After unbound proteins are removed by washing, the amount of bound marker can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the marker of interest is allowed to bind to the first antibody. The amount of the marker is quantitated by measuring the amount of a second antibody that binds the marker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for determining the presence or level of one or more biomarkers of immune response in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

Specific immunological binding of an antibody to one or more biomarkers of immune response can be detected directly or indirectly. Direct labels include fluorescent or luminescent tags, metals, dyes, radionuclides, and the like, attached to the antibody. An antibody labeled with iodine-125 ($^{125}$I) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.) or its current incarnation, such as BioSource, Invitrogen, or Life Technologies.

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

Quantitative Western blotting can also be used to detect or determine the presence or level of one or more biomarkers of immune response in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (Bio-Rad, Hercules, Calif.) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.*, 28:669-675 (1998).

Alternatively, a variety of immunohistochemical assay techniques can be used to determine the presence or level of one or more biomarkers of immune response in a sample. The term immunohistochemical assay encompasses techniques that utilize the visual detection of fluorescent dyes or enzymes coupled (i.e., conjugated) to antibodies that react with the marker of interest using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. An IFA assay, for example, is useful for determining whether a sample is positive for a biomarker, the level of biomarker in a sample, and/or a biomarker's staining pattern. The concentration of the biomarker in a sample can be quantitated, e.g., through endpoint titration or through measuring the visual intensity of fluorescence compared to a known reference standard.

In some embodiments, the concentration or level of a biomarker of immune response (e.g., a white blood cell, a cytokine, a protein produced in an inflammatory or immune response, or an antibody to a tumor cell surface marker) is measured by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, tandem MS, etc.). Qualitative or quantitative detection of a marker of interest can also be determined by well-known methods including, without limitation, Bradford assays, Coomassie blue staining, silver staining, assays for radiolabeled protein, and mass spectrometry.

In some embodiments, the concentration or level of a biomarker of immune response (e.g., a white blood cell, a cytokine, a protein produced in an inflammatory or immune response, or an antibody to a tumor cell surface marker) is measured by analysis of marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., *Current Protocols in Molecular Biology*, John Wiley & Sons, Inc. New York (1999), Chapter 7 and Supplement 47; Theophilus et al., "PCR Mutation Detection Protocols," Humana Press, (2002); and Innis et al., *PCR Protocols*, San Diego, Academic Press, Inc. (1990). General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

For the detection of a plurality of biomarkers (e.g., 2, 3, 4, 5, 6, 7, 8, 9, 10 or more biomarkers), the analysis of the biomarkers may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of markers on a single surface. Particularly useful physical formats comprise surfaces having a plurality of discrete, addressable locations for the detection of a plurality of different markers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection. Yet another suitable format for performing simultaneous assays of a plurality of markers is the Luminex MultiAnalyte Profiling (xMAP) technology, previously known as FlowMetrix and LabMAP (Elshal and McCoy, 2006), a multiplex bead-based flow cytometric assay that utilizes polystyrene beads that are internally dyed with different intensities of red and infrared fluorophores. The beads can be bound by various capture reagents such as antibodies, oligonucleotides, and peptides, therefore facilitating the quantification of various biomarkers such as proteins, ligands, DNA and RNA (Fulton et al., 1997; Kingsmore, 2006; Nolan and Mandy, 2006, Vignali, 2000; Ray et al., 2005).

Several biomarkers of interest may be combined into one test for efficient processing of a multiple of samples. In addition, one skilled in the art would recognize the value of testing multiple samples (e.g., at successive time points, etc.) from the same subject. For example, samples can be collected daily, weekly, monthly, or at other intervals from a subject and tested. Such testing of serial samples can allow the identification of changes in marker levels over time. Increases or decreases in marker levels, as well as the absence of change in marker levels, can also provide useful information to measure and/or quantify stimulation of immune response.

An immune booster can be administered in order to help create conditions for stimulating the immune systems. Natural and synthetic supplements that have been thought to be immune boosters at one time or another include flaxseed oil, sodium ascorbate (i.e., vitamin C), calcium ascorbate, magnesium ascorbate, potassium ascorbate, zinc ascorbate, manganese ascorbate, and chromium ascorbate, and cayenne pepper (*capsicum*), *astragalus, Echinacea*, esberitox, olive leaf extract, *sambucus* (elderberry), umcka, (umckaloabo), and zinc.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

As noted previously, all measurements, dimensions, and materials provided herein within the specification or within the figures are by way of example only.

A recitation of "a," "an," or "the" is intended to mean "one or more" unless specifically indicated to the contrary. Reference to a "first" component does not necessarily require that a second component be provided. Moreover reference to a "first" or a "second" component does not limit the referenced component to a particular location unless expressly stated.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

What is claimed is:

1. A method for stimulating an immune response to a disease in a subject, the method comprising:
    determining a target treatment energy based on a size and a type of a tumor in the subject;
    selecting or allowing selection of a number of pulses, an amplitude of at least 10 kilovolts per centimeter, or a pulse length of between 0.1 nanoseconds and 1000 nanoseconds for sub-microsecond pulsed electric fields based on the determined target treatment energy; and
    applying to the tumor, using a plurality of electrodes positioned in or around the tumor or a portion thereof, the sub-microsecond pulsed electric fields having the selected number of pulses, the selected amplitude, or the selected pulse length.

2. The method of claim 1 further comprising:
    adjusting the target treatment energy based on a comparison of a measured immune response biomarker before the applying and a measured immune response biomarker after the applying in a sample of the subject;
    determining a new number of pulses, a new amplitude, or a new pulse length based on the adjusted target treatment energy; and
    treating the tumor again by:
        applying to the tumor, using the plurality of electrodes, sub-microsecond pulsed electric fields based on the new determined number of pulses, the new determined amplitude, or the new determined pulse length.

3. The method of claim 1, wherein the method is used in combination with introducing cluster of differentiation 47 (CD47)-blocking antibodies into the subject, the CD47-blocking antibodies neutralizing CD47 on surface membranes of tumor cells of the tumor.

4. The method of claim 3, wherein the introducing of CD47-blocking antibodies occurs before the applying of the sub-microsecond pulsed electric fields.

5. The method of claim 1, wherein the method is used in combination with injecting doxorubicin into the subject.

6. The method of claim 1, wherein the method is used in combination with injecting cytotoxic T-lymphocyte antigen 4 (CTLA-4)-blocking antibodies into the subject.

7. The method of claim 1, wherein the method is used in combination with injecting programmed death 1 (PD-1)-blocking antibodies into the subject.

8. The method of claim 1, the method further comprising obtaining a measurement of an immune response biomarker in a sample of the subject, wherein the measurement is based on a concentration or level of white blood cells in the sample.

9. The method of claim 8, wherein the measured white blood cells include cluster of differentiation 4+(CD4+) or cluster of differentiation 8+(CD8+) T lymphocytes.

10. The method of claim 2, wherein the gauged immune response biomarker is based on:
    measuring a concentration or level in the sample of a member selected from a group consisting of white blood cells, inflammatory cytokines, C-reactive proteins, and antibodies of cancer cell markers.

11. The method of claim 1, wherein the tumor is selected among multiple tumors in the subject based on an accessibility of locations and measured sizes of the multiple tumors.

12. The method of claim 11 wherein the accessibility of each tumor is determined by identifying pathways to opposed sides of a respective tumor that can be contacted by electrodes through pierceable paths in the subject.

13. The method of claim 1, wherein the method reduces metastasis of the disease in the subject.

14. The method of claim 1, wherein the tumor is cancerous, precancerous, or non-cancerous.

15. The method of claim 1, wherein one or more of the number of pulses, the amplitude, or the pulse length are inputted though a user interface.

16. The method of claim 1, the method comprises obtaining a measurement of an immune response biomarker, wherein the measurement is automated.

17. The method of claim 1, wherein the disease is one or more of the following cancers: digestive, gastrointestinal, colorectal, gastrointestinal stromal, colon, rectal, anal, bile duct, small intestine, esophageal, breast, lung, gallbladder, liver, pancreatic, appendix, prostate, ovarian, renal, cancer of the central nervous system, skin, lymphomas, gliomas, choriocarcinomas, head and neck, osteogenic sarcomas, or blood cancers.

18. The method of claim 1, the method further comprising:
    detecting calreticulin on surface membranes of cells of the tumor after the applying.

19. The method of claim 1, wherein the selected number of pulses is greater than 50.

20. A machine-readable tangible medium storing instructions for causing one or more machines to execute operations for:
    determining a target treatment energy based on a size and a type of a tumor in a subject;
    selecting a number of pulses, an amplitude of at least 10 kilovolts per centimeter, or a pulse length of between 0.1 nanoseconds and 1000 nanoseconds for sub-microsecond pulsed electric fields based on the determined target treatment energy; and
    applying to the tumor, through a set of electrodes, the sub-microsecond pulsed electric fields having the selected number of pulses, the selected amplitude, or the selected pulse length.

21. The medium of claim 20, further comprising instructions for:
    selecting a repetition frequency of the sub-microsecond pulsed electric fields based at least on the determined size and type of the tumor.

22. The medium of claim 20, wherein the tumor is cancerous, precancerous, or non-cancerous.

* * * * *